United States Patent
Ravikumar et al.

(10) Patent No.: US 9,326,757 B2
(45) Date of Patent: May 3, 2016

(54) SURGICAL INSTRUMENTS FOR LAPAROSCOPIC ASPIRATION AND RETRACTION

(75) Inventors: Sundaram Ravikumar, Briarcliff Manor, NY (US); Allan Alward, Shelton, CT (US)

(73) Assignee: TELEFLEX MEDICAL INCORPORATED, Morrisville, NC (US)

( * ) Notice: Subject to any disclaimer, the term of this patent is extended or adjusted under 35 U.S.C. 154(b) by 600 days.

(21) Appl. No.: 12/862,917

(22) Filed: Aug. 25, 2010

(65) Prior Publication Data

US 2011/0160538 A1  Jun. 30, 2011

Related U.S. Application Data

(60) Provisional application No. 61/291,842, filed on Dec. 31, 2009, provisional application No. 61/323,359, filed on Apr. 13, 2010.

(51) Int. Cl.
| | |
|---|---|
| *A61B 17/02* | (2006.01) |
| *A61B 17/00* | (2006.01) |
| *A61B 17/22* | (2006.01) |
| *A61B 17/34* | (2006.01) |

(52) U.S. Cl.
CPC ....... *A61B 17/00234* (2013.01); *A61B 17/0218* (2013.01); *A61B 17/0057* (2013.01); *A61B 2017/00349* (2013.01); *A61B 2017/00637* (2013.01); *A61B 2017/00986* (2013.01); *A61B 2017/22054* (2013.01); *A61B 2017/22069* (2013.01); *A61B 2017/3488* (2013.01)

(58) Field of Classification Search
CPC ................ A61B 17/0218; A61B 2017/00349; A61B 2017/00637; A61B 2017/00986; A61B 2017/22051; A61B 2017/22069; A61B 2017/348–2017/3488
USPC .......................... 600/201–249; 606/246–279
See application file for complete search history.

(56) References Cited

U.S. PATENT DOCUMENTS

| | | | |
|---|---|---|---|
| 1,527,291 | A | 2/1925 | Zorraquin |
| 2,623,521 | A | 12/1952 | Shaw |
| 2,630,803 | A | 3/1953 | Baran |
| 2,890,801 | A | 6/1959 | Ladd et al. |
| 3,068,739 | A | 12/1962 | Hicks, Jr. et al. |

(Continued)

FOREIGN PATENT DOCUMENTS

| | | |
|---|---|---|
| EP | 449663 A2 | 10/1991 |
| WO | WO-2007106813 A2 | 9/2007 |

OTHER PUBLICATIONS

International Search Report and Written Opinion for PCT/US2010/053707 issued May 9, 2011.

(Continued)

*Primary Examiner* — Nicholas Plionis
(74) *Attorney, Agent, or Firm* — Baker and Hostetler LLP

(57) ABSTRACT

Various surgical instruments for laparoscopic procedures are provided for aspirating and retracting a hollow organ such as a gallbladder. The surgical instruments include a needle body and an anchor coupled to the needle body. The anchor is adapted and configured for engaging and retracting the hollow organ, and can be held and deployed from within the needle body or from an outside surface of the needle body. The needle body defines an aperture for permitting aspiration of contents of the hollow organ.

34 Claims, 29 Drawing Sheets

(56) References Cited

U.S. PATENT DOCUMENTS

| | | |
|---|---|---|
| 3,530,492 A | 9/1970 | Ferber |
| 3,817,251 A | 6/1974 | Hasson |
| 3,840,008 A | 10/1974 | Noiles |
| 3,844,291 A | 10/1974 | Moen |
| 3,857,386 A | 12/1974 | Ashbell |
| 3,938,527 A | 2/1976 | Rioux et al. |
| 3,941,121 A | 3/1976 | Olinger et al. |
| 3,967,625 A | 7/1976 | Yoon |
| 3,982,533 A | 9/1976 | Wiest |
| 4,016,881 A | 4/1977 | Rioux et al. |
| 4,077,412 A | 3/1978 | Moossun |
| 4,174,715 A | 11/1979 | Hasson |
| 4,177,814 A | 12/1979 | Knepshield et al. |
| 4,180,068 A | 12/1979 | Jacobsen et al. |
| 4,193,198 A | 3/1980 | Bauer |
| 4,254,762 A | 3/1981 | Yoon |
| 4,269,192 A | 5/1981 | Matsuo |
| 4,299,230 A | 11/1981 | Kubota |
| 4,311,138 A | 1/1982 | Sugarman |
| 4,517,965 A | 5/1985 | Ellison |
| 4,535,773 A | 8/1985 | Yoon |
| 4,550,715 A | 11/1985 | Santangelo et al. |
| 4,570,642 A | 2/1986 | Kane et al. |
| 4,573,452 A | 3/1986 | Greenberg |
| 4,607,619 A | 8/1986 | Seike et al. |
| 4,624,243 A | 11/1986 | Lowery et al. |
| 4,653,475 A | 3/1987 | Seike et al. |
| D293,470 S | 12/1987 | Adler |
| 4,867,404 A | 9/1989 | Harrington et al. |
| 4,869,717 A | 9/1989 | Adair |
| 4,874,375 A | 10/1989 | Ellison |
| 4,949,927 A | 8/1990 | Madocks et al. |
| 5,062,847 A | 11/1991 | Barnes |
| 5,071,419 A | 12/1991 | Rydell et al. |
| 5,073,169 A | 12/1991 | Raiken |
| 5,098,388 A | 3/1992 | Kulkashi et al. |
| 5,100,402 A | 3/1992 | Fan |
| 5,104,381 A | 4/1992 | Gresl et al. |
| 5,137,509 A | 8/1992 | Freitas |
| 5,139,485 A | 8/1992 | Smith et al. |
| 5,147,316 A | 9/1992 | Castillenti |
| 5,171,311 A | 12/1992 | Rydell et al. |
| 5,176,128 A | 1/1993 | Andrese |
| 5,176,643 A | 1/1993 | Kramer et al. |
| 5,176,697 A | 1/1993 | Hasson et al. |
| 5,197,948 A | 3/1993 | Ghodsian |
| 5,199,944 A | 4/1993 | Cosmescu |
| 5,201,742 A | 4/1993 | Hasson |
| 5,201,752 A | 4/1993 | Brown et al. |
| 5,222,973 A | 6/1993 | Sharpe et al. |
| 5,224,954 A | 7/1993 | Watts et al. |
| 5,226,426 A | 7/1993 | Yoon |
| 5,235,966 A | 8/1993 | Jamner |
| 5,246,426 A | 9/1993 | Lewis et al. |
| 5,256,148 A | 10/1993 | Smith et al. |
| 5,261,891 A | 11/1993 | Brinkerhoff et al. |
| 5,261,905 A | 11/1993 | Doresey, III |
| 5,271,385 A | 12/1993 | Bailey |
| 5,284,130 A | 2/1994 | Ratliff |
| 5,290,276 A | 3/1994 | Sewell, Jr. |
| 5,292,310 A | 3/1994 | Yoon |
| 5,308,327 A | 5/1994 | Heaven et al. |
| 5,318,040 A | 6/1994 | Kensey et al. |
| 5,320,627 A | 6/1994 | Sorensen et al. |
| 5,330,497 A | 7/1994 | Freitas et al. |
| 5,339,801 A | 8/1994 | Poloyko et al. |
| 5,342,357 A | 8/1994 | Nardella |
| 5,350,356 A | 9/1994 | Bales et al. |
| 5,353,812 A | 10/1994 | Chow |
| 5,354,283 A | 10/1994 | Bark et al. |
| 5,370,109 A | 12/1994 | Cuny |
| 5,370,134 A | 12/1994 | Chin et al. |
| 5,375,588 A | 12/1994 | Yoon |
| 5,383,886 A | 1/1995 | Kensey et al. |
| 5,417,697 A | 5/1995 | Wilk et al. |
| 5,421,821 A | 6/1995 | Janicki et al. |
| 5,425,357 A | 6/1995 | Moll et al. |
| 5,429,598 A | 7/1995 | Waxman et al. |
| 5,431,173 A | 7/1995 | Chin et al. |
| 5,437,266 A | 8/1995 | McPherson et al. |
| 5,437,647 A | 8/1995 | Firth et al. |
| 5,439,476 A | 8/1995 | Frantzides |
| 5,499,997 A | 3/1996 | Sharpe et al. |
| 5,505,710 A | 4/1996 | Dorsey, III |
| 5,514,087 A | 5/1996 | Jones |
| 5,514,111 A | 5/1996 | Phelps |
| 5,520,697 A | 5/1996 | Lindenberg et al. |
| 5,527,264 A | 6/1996 | Moll et al. |
| 5,538,008 A | 7/1996 | Crowe |
| 5,556,411 A | 9/1996 | Taoda et al. |
| 5,569,291 A | 10/1996 | Privitera et al. |
| 5,571,137 A | 11/1996 | Marlow et al. |
| 5,573,496 A | 11/1996 | McPherson et al. |
| 5,578,030 A | 11/1996 | Levin |
| 5,578,031 A | 11/1996 | Wilk et al. |
| 5,586,991 A | 12/1996 | Yoon |
| 5,588,951 A | 12/1996 | Zhu et al. |
| 5,599,292 A | 2/1997 | Yoon |
| 5,613,937 A | 3/1997 | Garrison et al. |
| 5,618,306 A | 4/1997 | Roth et al. |
| 5,626,597 A | 5/1997 | Urban et al. |
| 5,634,918 A | 6/1997 | Richards |
| 5,658,272 A | 8/1997 | Hasson |
| 5,669,883 A | 9/1997 | Scarfone et al. |
| 5,676,156 A | 10/1997 | Yoon |
| D388,515 S | 12/1997 | Bookwalter et al. |
| 5,695,462 A | 12/1997 | Sutcu et al. |
| D389,242 S | 1/1998 | Bookwalter et al. |
| D389,913 S | 1/1998 | Bookwalter et al. |
| 5,707,362 A | 1/1998 | Yoon |
| 5,725,504 A | 3/1998 | Collins |
| 5,775,334 A | 7/1998 | Lamb et al. |
| 5,779,680 A | 7/1998 | Yoon |
| 5,803,902 A | 9/1998 | Sienkiewicz et al. |
| 5,807,402 A | 9/1998 | Yoon |
| 5,810,866 A | 9/1998 | Yoon |
| 5,813,976 A | 9/1998 | Filipi et al. |
| 5,823,945 A | 10/1998 | Moll et al. |
| 5,827,221 A | 10/1998 | Phelps |
| 5,827,315 A | 10/1998 | Yoon |
| 5,846,191 A | 12/1998 | Wells et al. |
| 5,857,999 A | 1/1999 | Quick et al. |
| 5,860,987 A | 1/1999 | Ratcliff et al. |
| 5,865,780 A | 2/1999 | Tuite |
| 5,871,453 A | 2/1999 | Banik et al. |
| 5,882,340 A | 3/1999 | Yoon |
| 5,893,873 A | 4/1999 | Rader et al. |
| 5,899,425 A | 5/1999 | Corey Jr. et al. |
| 5,906,620 A | 5/1999 | Nakao et al. |
| 5,919,163 A | 7/1999 | Glickman |
| 5,921,918 A | 7/1999 | Riza |
| 5,921,919 A | 7/1999 | Chin et al. |
| 5,928,140 A | 7/1999 | Hardten |
| 5,951,488 A | 9/1999 | Slater et al. |
| 5,951,574 A | 9/1999 | Stefanchik et al. |
| 5,964,223 A | 10/1999 | Baran |
| 5,964,698 A | 10/1999 | Fowler |
| 6,051,008 A | 4/2000 | Saadat et al. |
| 6,051,088 A | 4/2000 | Muckle et al. |
| D426,883 S | 6/2000 | Berman et al. |
| 6,090,042 A | 7/2000 | Rullo et al. |
| 6,099,550 A | 8/2000 | Yoon |
| 6,110,127 A | 8/2000 | Suzuki |
| 6,155,439 A | 12/2000 | Draughn |
| 6,165,184 A | 12/2000 | Verdura et al. |
| 6,190,311 B1 | 2/2001 | Glines et al. |
| 6,197,002 B1 | 3/2001 | Peterson |
| 6,200,263 B1 | 3/2001 | Person |
| 6,228,059 B1 | 5/2001 | Astarita |
| 6,248,062 B1 | 6/2001 | Adler et al. |
| 6,258,107 B1 | 7/2001 | Balazs et al. |
| 6,319,266 B1 | 11/2001 | Stellon et al. |
| 6,322,578 B1 | 11/2001 | Houle et al. |
| 6,332,866 B1 | 12/2001 | Grieshaber et al. |

(56) References Cited

U.S. PATENT DOCUMENTS

| | | | |
|---|---|---|---|
| 6,391,046 B1 | 5/2002 | Overaker et al. |
| 6,428,503 B1 | 8/2002 | Kierce |
| 6,488,691 B1 | 12/2002 | Carroll et al. |
| 6,504,985 B2 | 1/2003 | Parker et al. |
| 6,561,974 B1 | 5/2003 | Grieshaber et al. |
| 6,610,009 B2 | 8/2003 | Person |
| 6,616,683 B1 | 9/2003 | Toth et al. |
| 6,620,129 B2 | 9/2003 | Stecker et al. |
| 6,630,103 B2 | 10/2003 | Martin et al. |
| 6,632,170 B1 | 10/2003 | Bohanan et al. |
| 6,648,839 B2 | 11/2003 | Manna et al. |
| 6,736,814 B2 | 5/2004 | Manna et al. |
| 6,743,237 B2 | 6/2004 | Dhindsa |
| 6,761,718 B2 | 7/2004 | Madsen |
| 6,830,578 B2 | 12/2004 | O'Heeron et al. |
| 6,832,984 B2 | 12/2004 | Stelzer et al. |
| 6,855,156 B2 | 2/2005 | Etter et al. |
| 6,860,894 B1 | 3/2005 | Pittman |
| 6,899,704 B2 | 5/2005 | Sterman et al. |
| 6,902,536 B2 | 6/2005 | Manna et al. |
| 6,905,489 B2 | 6/2005 | Mantell et al. |
| 6,908,454 B2 | 6/2005 | McFarlane |
| 6,945,984 B2 | 9/2005 | Arumi et al. |
| 6,989,003 B2 | 1/2006 | Wing et al. |
| 7,001,333 B2 | 2/2006 | Hamel et al. |
| 7,041,055 B2 | 5/2006 | Young et al. |
| 7,066,879 B2 | 6/2006 | Fowler et al. |
| 7,083,617 B2 | 8/2006 | Kortenbach et al. |
| 7,112,172 B2 | 9/2006 | Orban, III et al. |
| 7,169,156 B2 | 1/2007 | Hart |
| 7,179,225 B2 | 2/2007 | Shluzas et al. |
| 7,223,267 B2 | 5/2007 | Isola et al. |
| 7,247,149 B2 | 7/2007 | Beyerlein |
| 7,331,970 B2 | 2/2008 | Almodovar |
| 7,449,011 B2 | 11/2008 | Wenchell et al. |
| 7,481,766 B2 | 1/2009 | Lee et al. |
| 7,597,701 B2 | 10/2009 | Hueil et al. |
| 7,615,067 B2 | 11/2009 | Lee et al. |
| 7,766,937 B2 | 8/2010 | Ravikumar |
| 2001/0005787 A1 | 6/2001 | Oz et al. |
| 2002/0137988 A1 | 9/2002 | Shipp et al. |
| 2003/0050613 A1 | 3/2003 | Hammerslag |
| 2003/0130693 A1 | 7/2003 | Levin et al. |
| 2003/0145864 A1 | 8/2003 | Dawson |
| 2005/0080435 A1 | 4/2005 | Smith et al. |
| 2005/0113737 A1 | 5/2005 | Ashby et al. |
| 2005/0113760 A1 | 5/2005 | Chachques et al. |
| 2005/0177182 A1* | 8/2005 | van der Burg et al. ........ 606/157 |
| 2005/0234507 A1 | 10/2005 | Geske et al. |
| 2007/0010715 A1 | 1/2007 | Sixto et al. |
| 2007/0135679 A1 | 6/2007 | Hunt et al. |
| 2007/0208374 A1* | 9/2007 | Boyle et al. .................... 606/200 |
| 2007/0213595 A1 | 9/2007 | Ravikumar |
| 2007/0213766 A1 | 9/2007 | Ravikumar |
| 2007/0213767 A1 | 9/2007 | Ravikumar |
| 2007/0250112 A1 | 10/2007 | Ravikumar et al. |
| 2007/0270640 A1 | 11/2007 | Dimitriou et al. |
| 2007/0277815 A1 | 12/2007 | Ravikumar et al. |
| 2007/0282170 A1 | 12/2007 | Ravikumar |
| 2007/0288033 A1* | 12/2007 | Murature et al. ............. 606/106 |
| 2007/0299387 A1 | 12/2007 | Williams et al. |
| 2008/0086166 A1 | 4/2008 | Ravikumar |
| 2008/0214957 A1* | 9/2008 | Verra et al. ..................... 600/578 |
| 2008/0234550 A1* | 9/2008 | Hawkes et al. ................ 600/204 |
| 2009/0048585 A1 | 2/2009 | Noda et al. |
| 2009/0149857 A1 | 6/2009 | Culbert et al. |
| 2009/0259225 A1 | 10/2009 | Ravikumar et al. |
| 2009/0292323 A1* | 11/2009 | Chirico et al. ............... 606/86 R |
| 2009/0306466 A1 | 12/2009 | Bonadio et al. |
| 2009/0306471 A1 | 12/2009 | Gettman |
| 2010/0016884 A1 | 1/2010 | Ravikumar |
| 2010/0185179 A1* | 7/2010 | Chan ............................ 604/508 |
| 2010/0292724 A1 | 11/2010 | Ravikumar et al. |

OTHER PUBLICATIONS

International Search Report for PCT/US07/63883.
International Search Report for PCT/US07/80938.
Cauterization, Wikipedia entry, Apr. 5, 2011 (3 pages) http://en.wikipedia.org/wiki/Cauterization.
Needlescopic Cholecystectomy, Procedure Profile, California Pacific Medical Center.

* cited by examiner

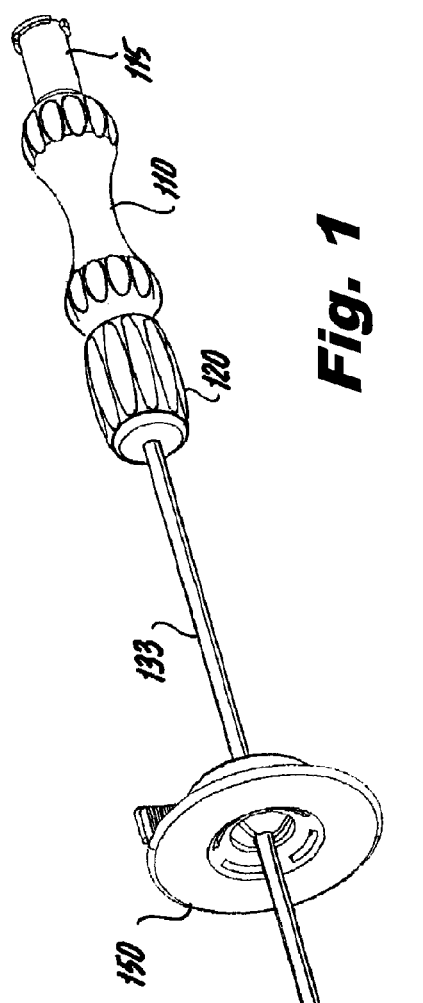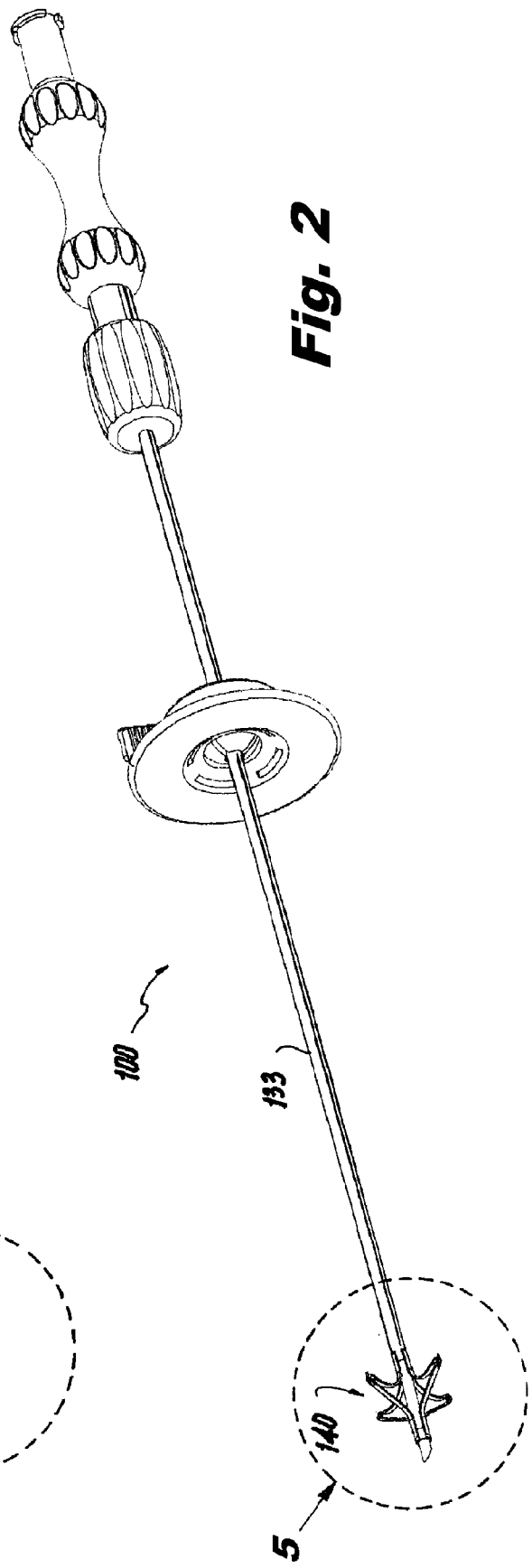

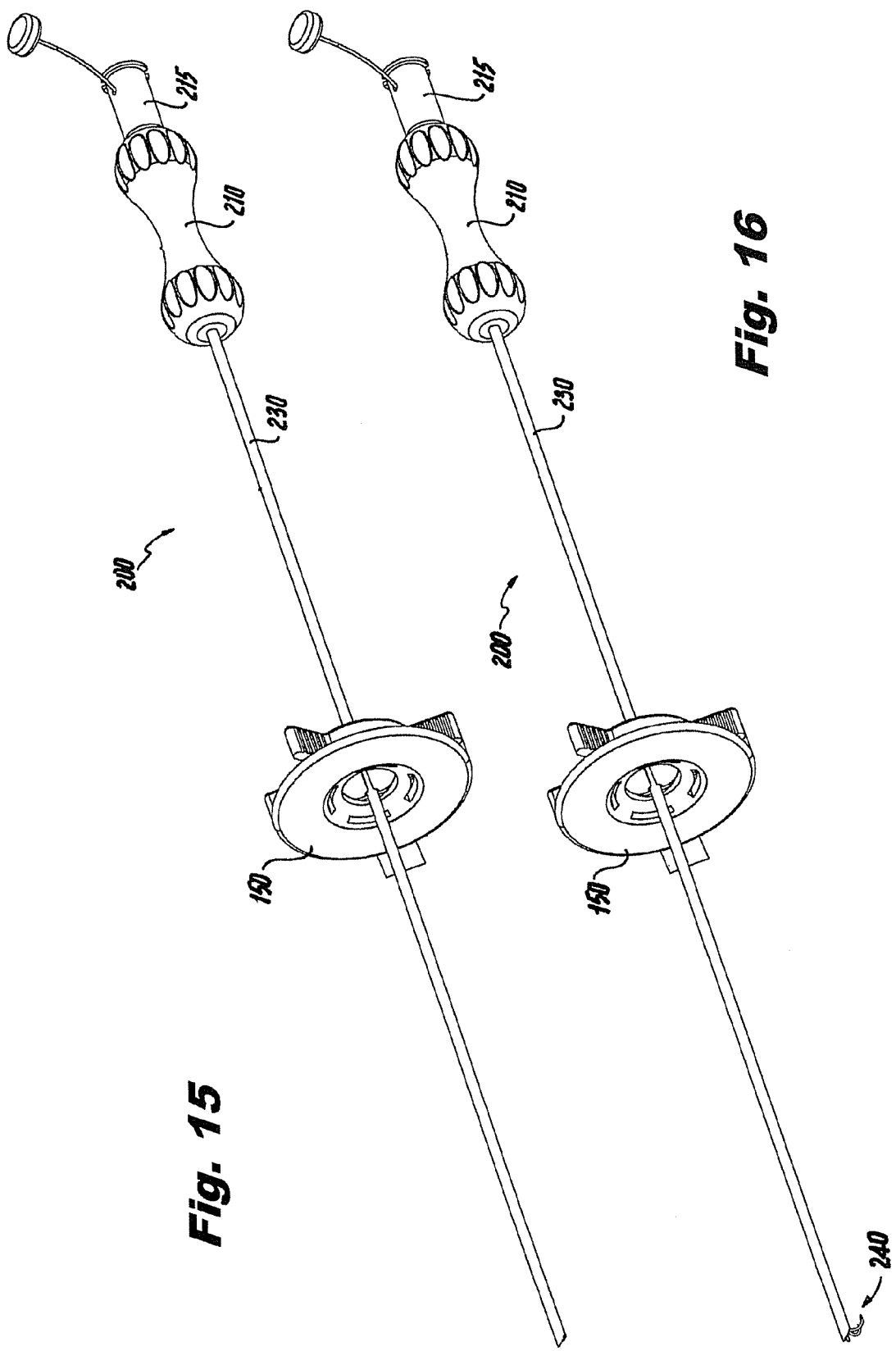

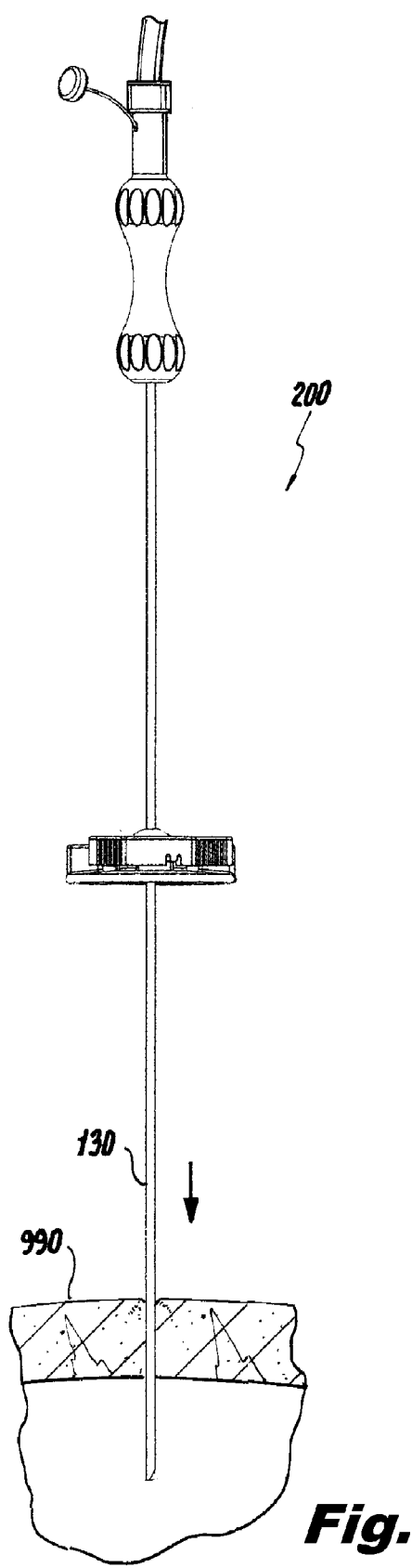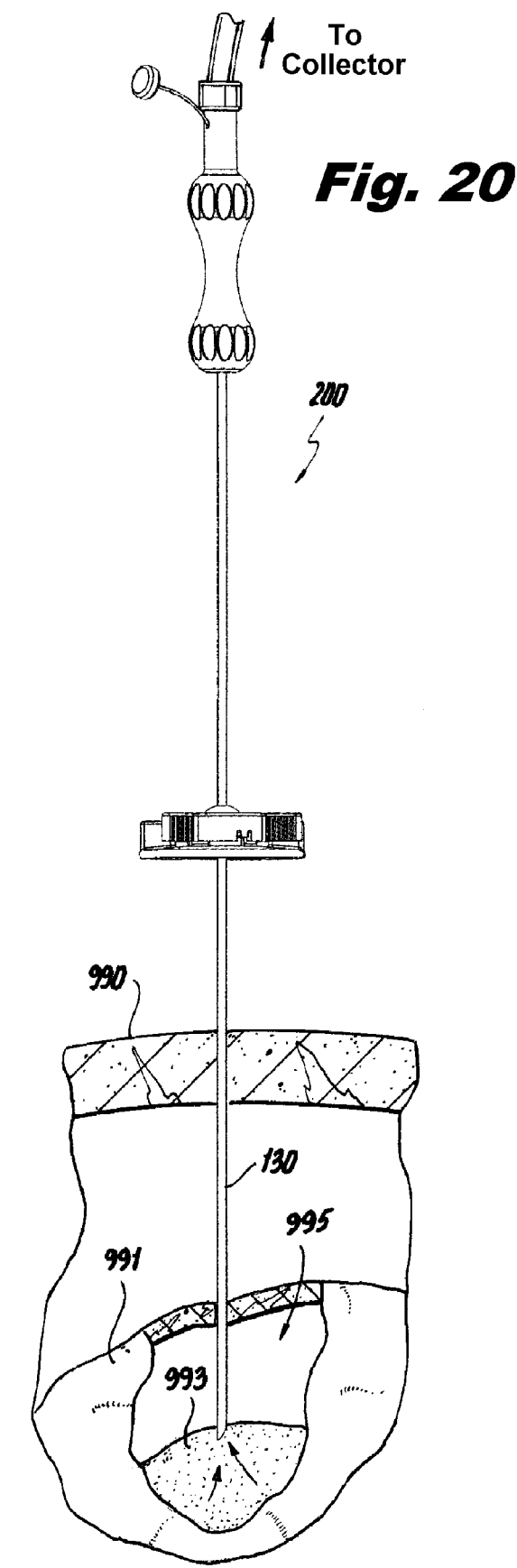
Fig. 19
Fig. 20

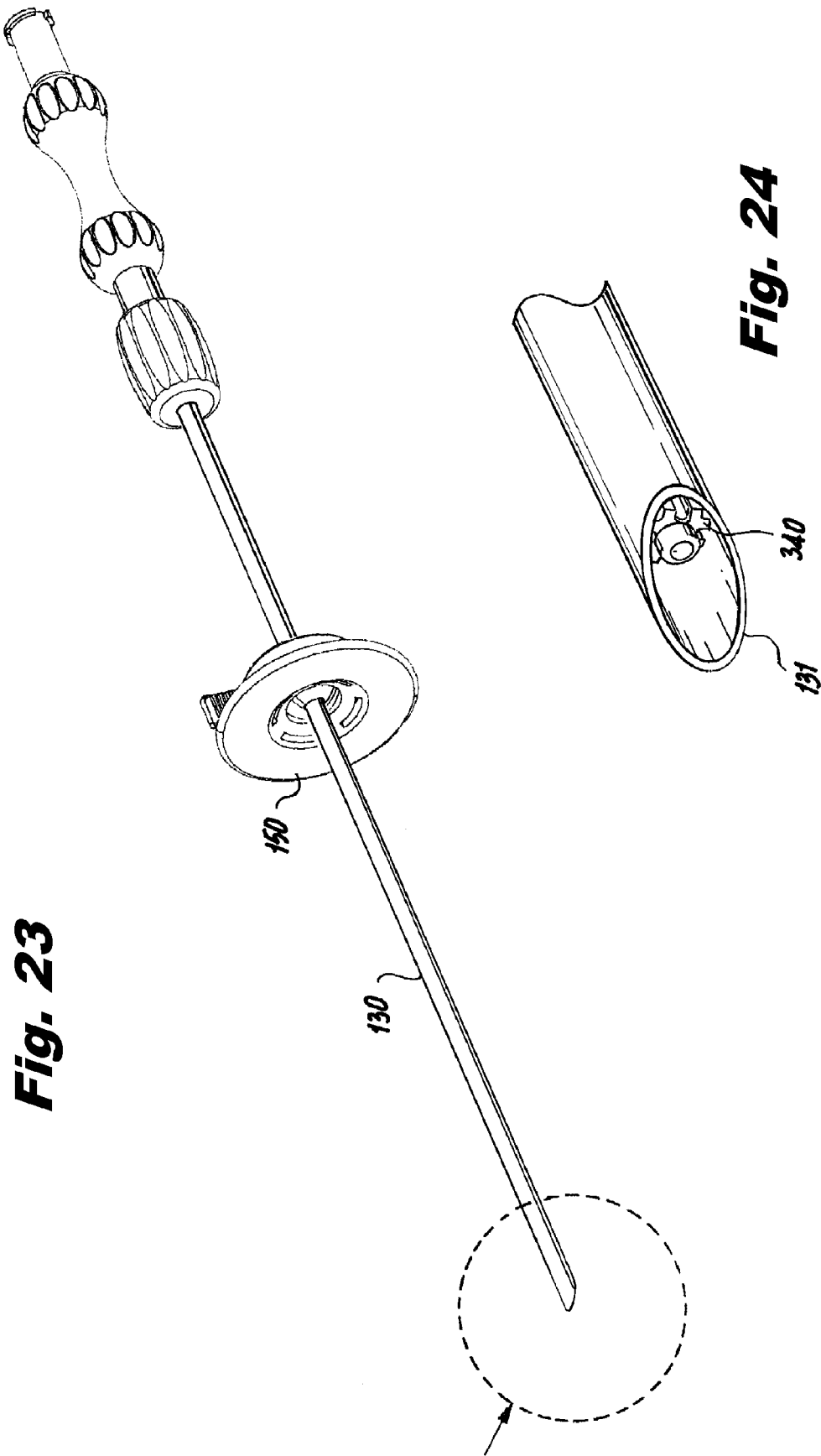

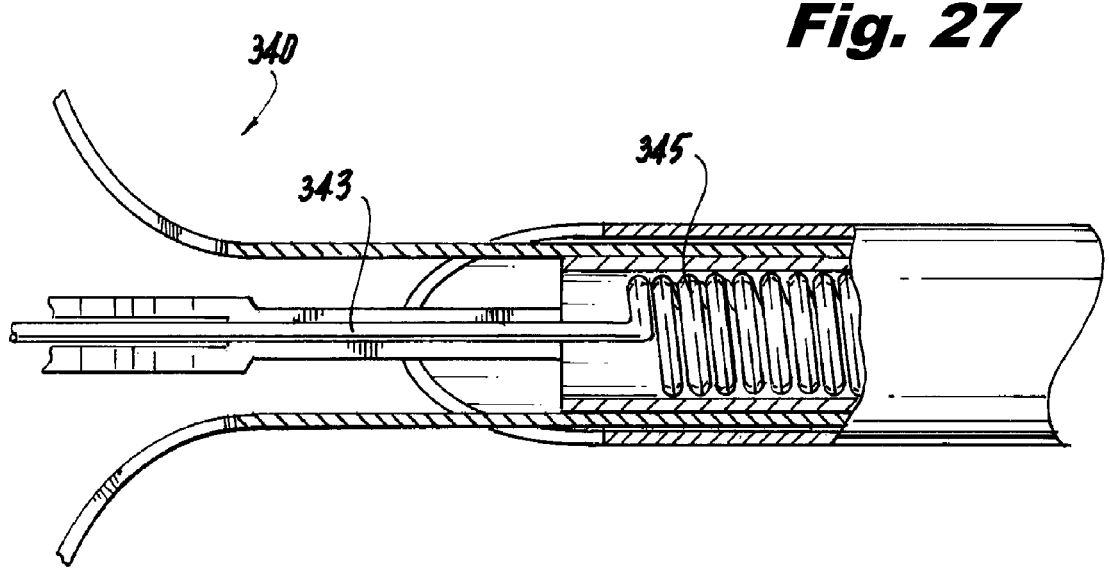
*Fig. 27*
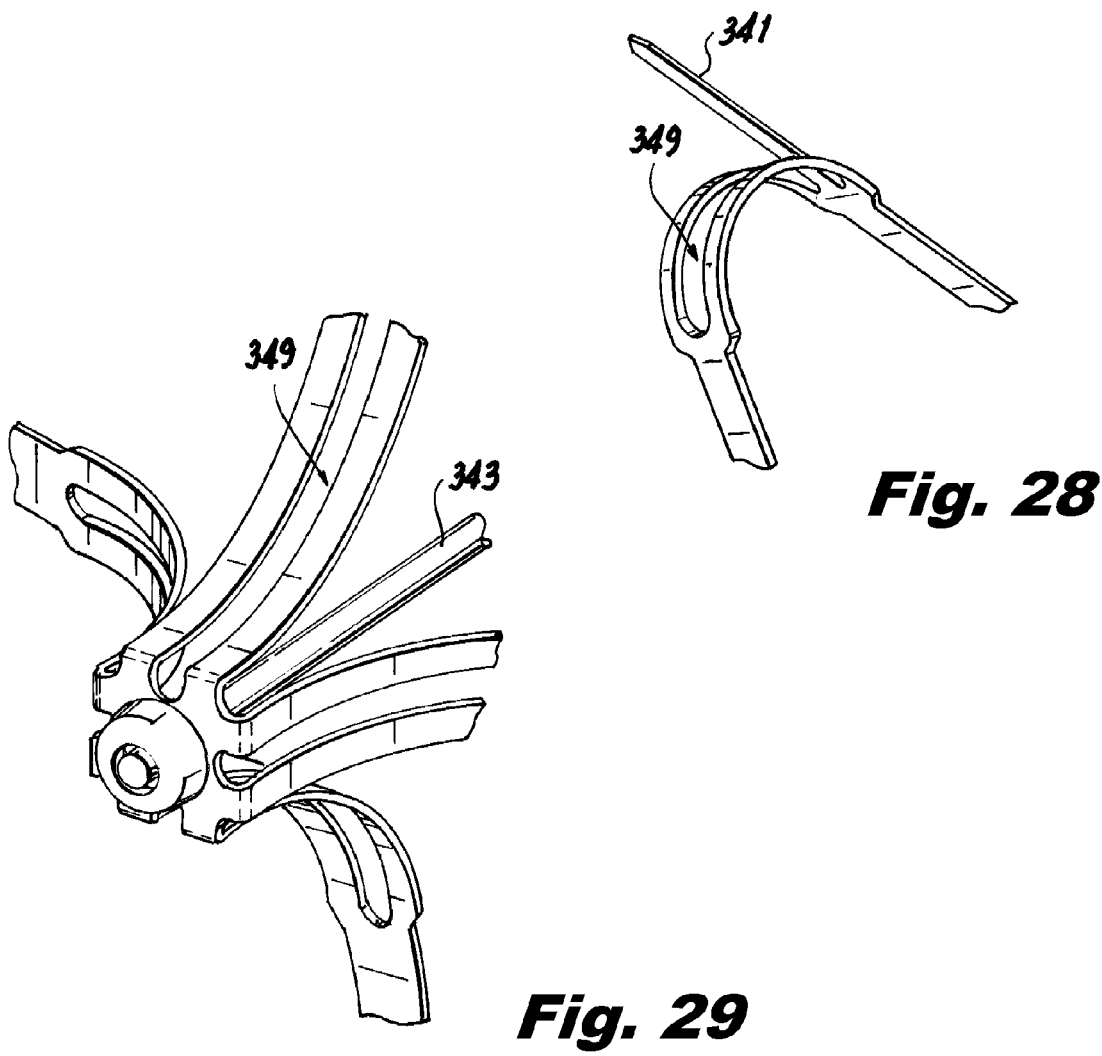
*Fig. 28*
*Fig. 29*

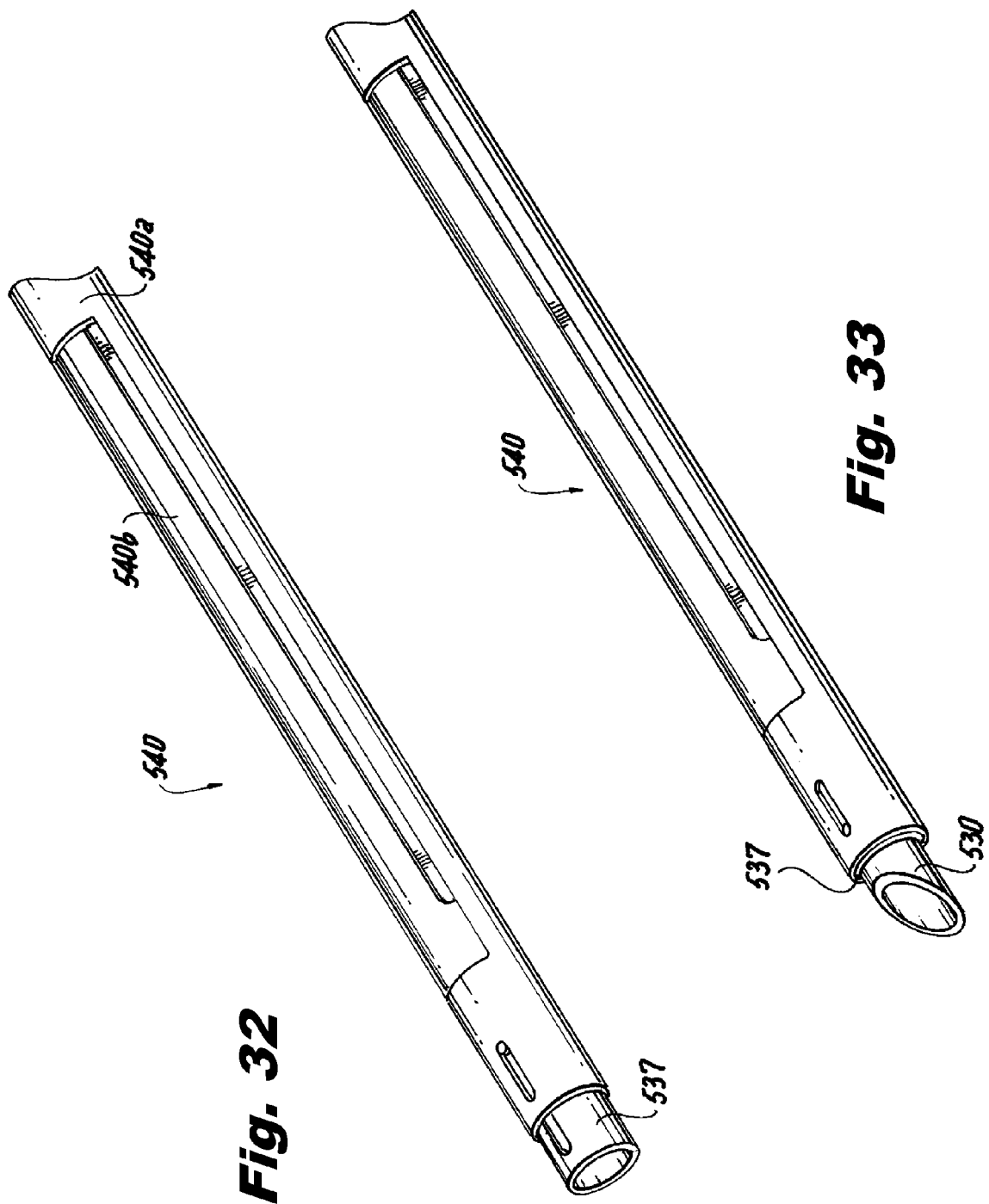

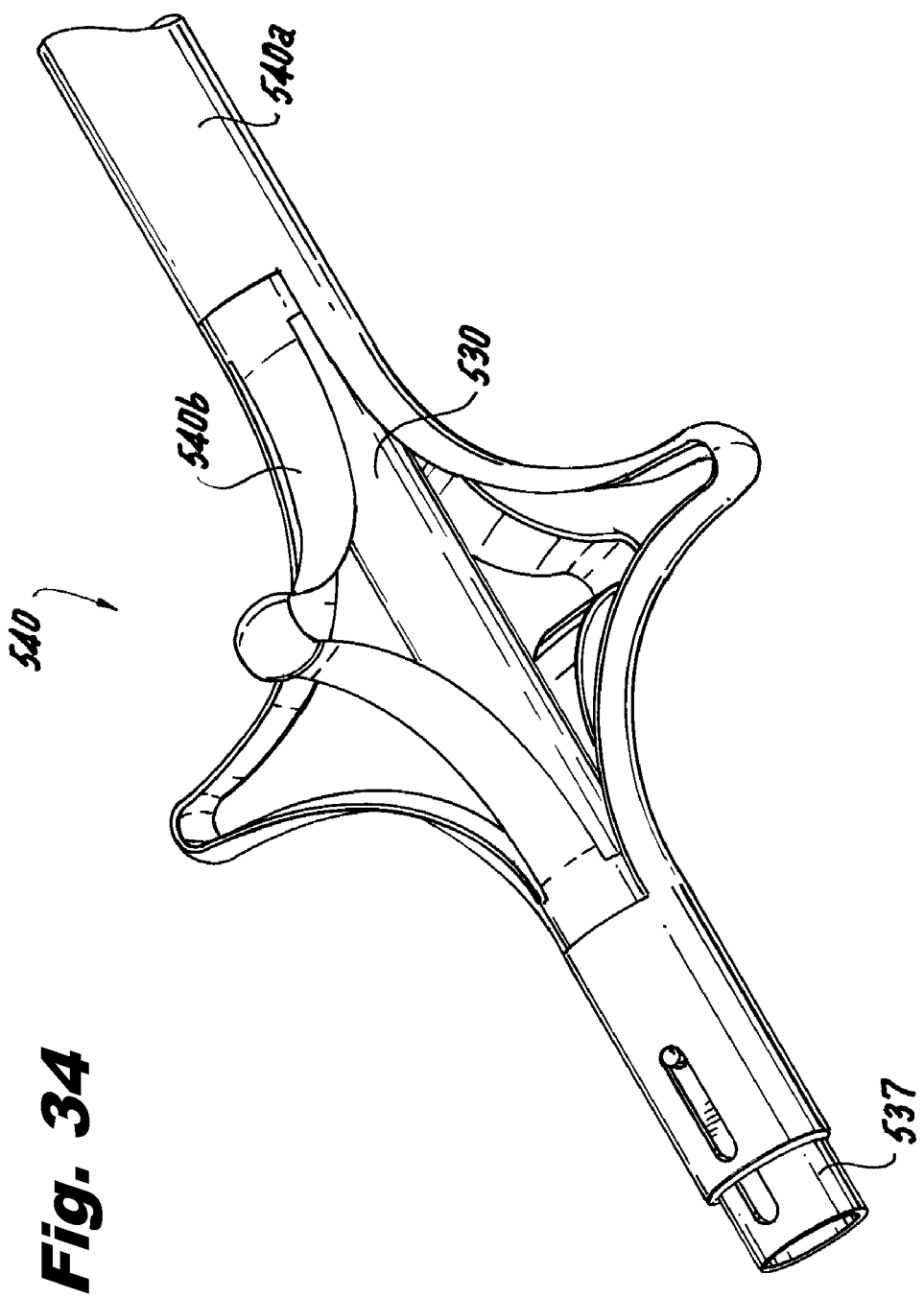

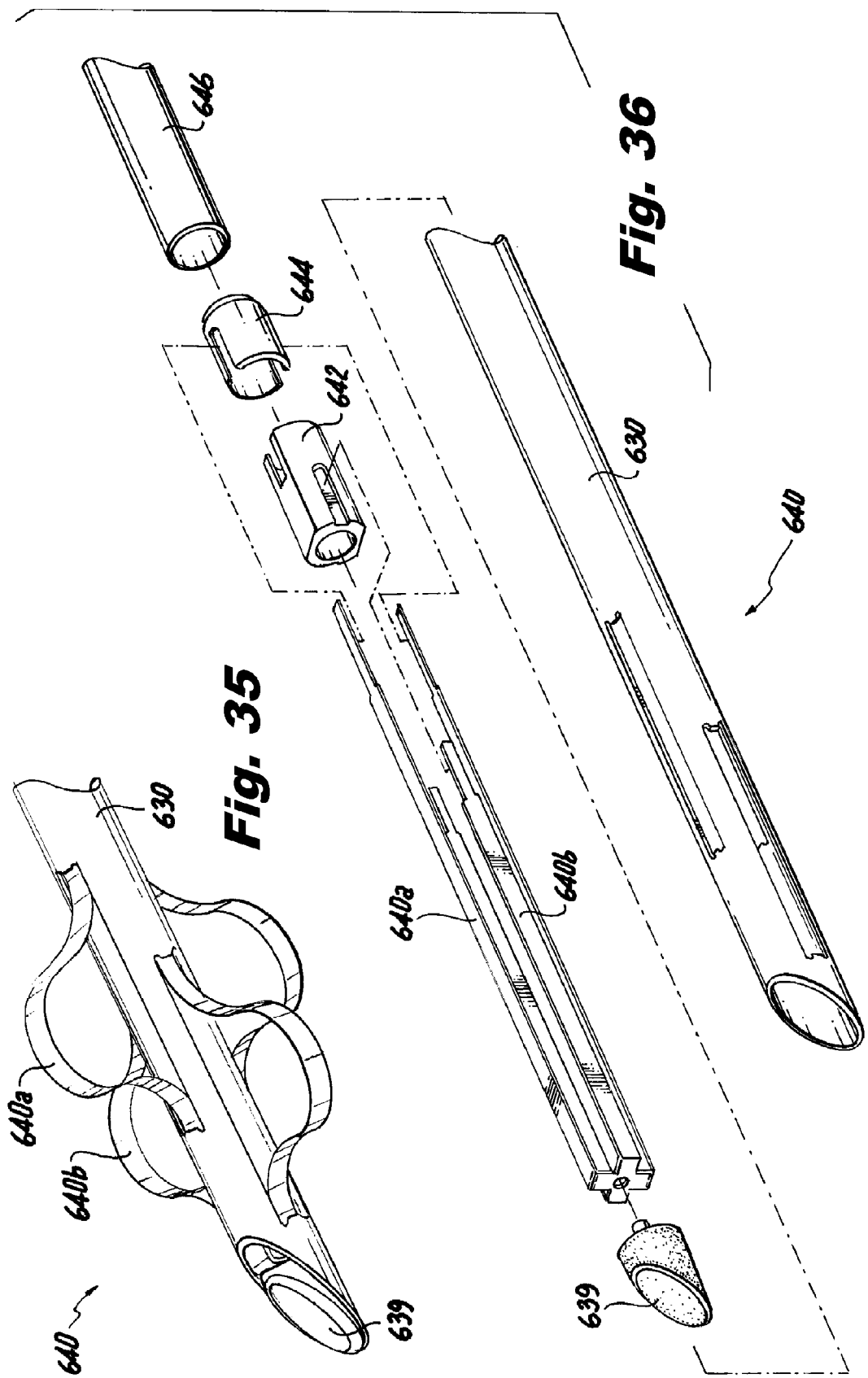

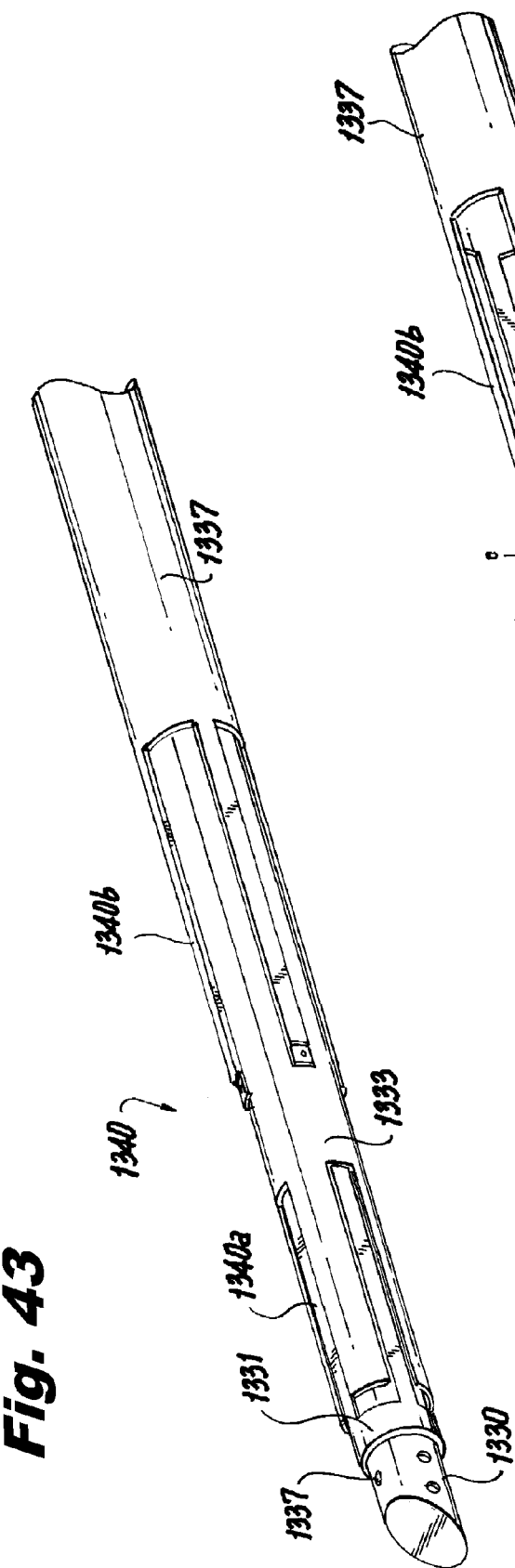
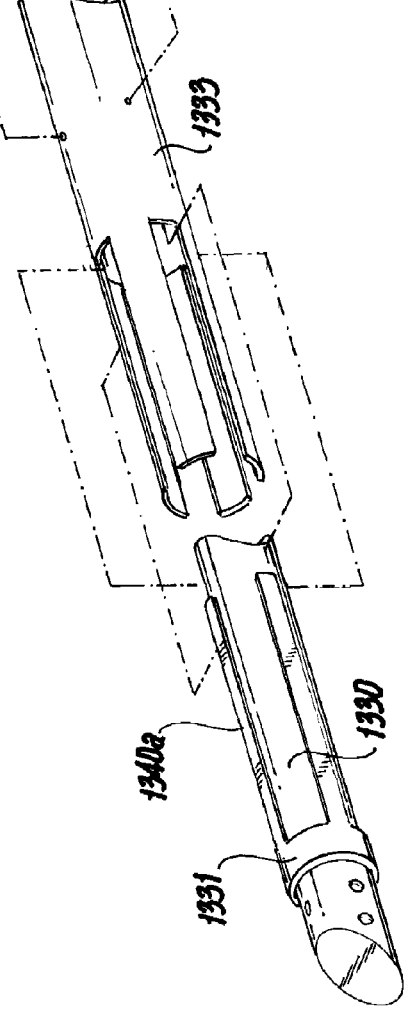
Fig. 43
Fig. 44

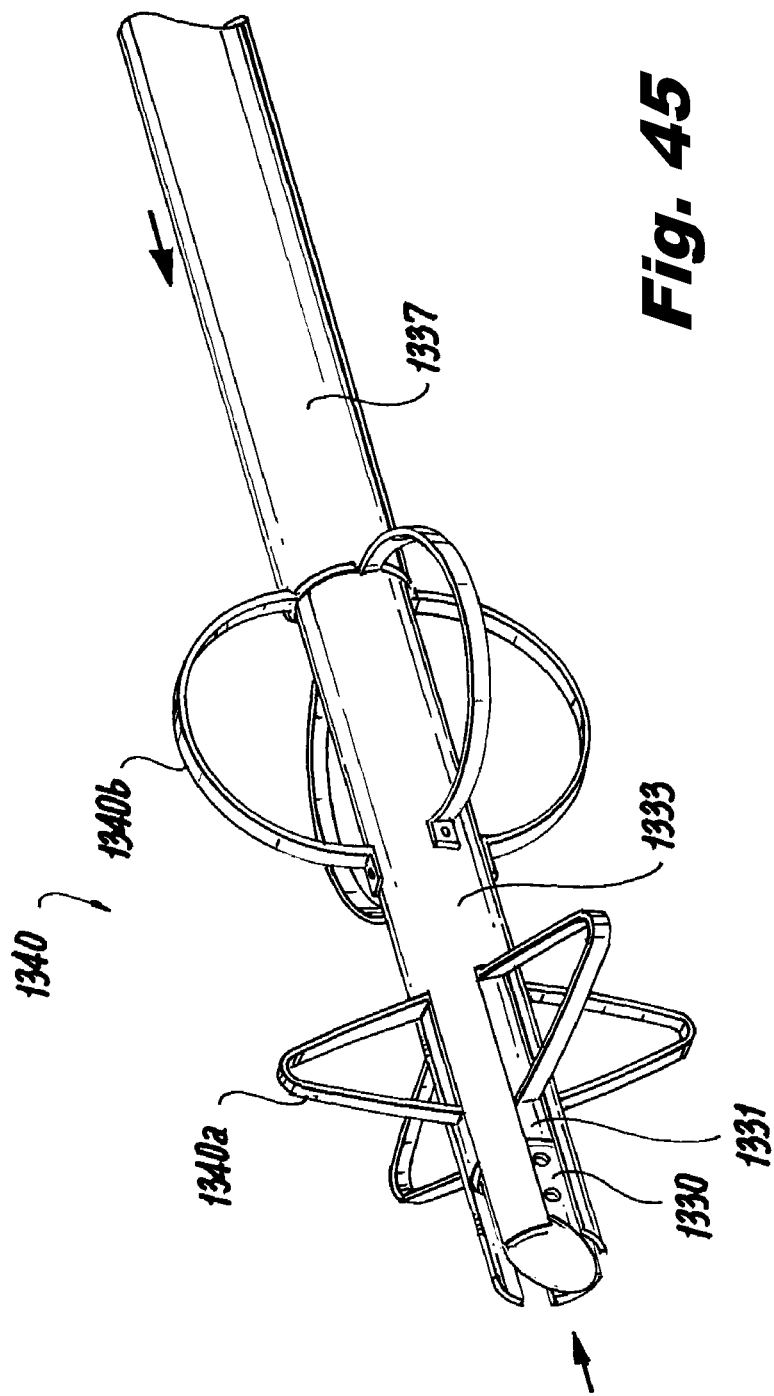

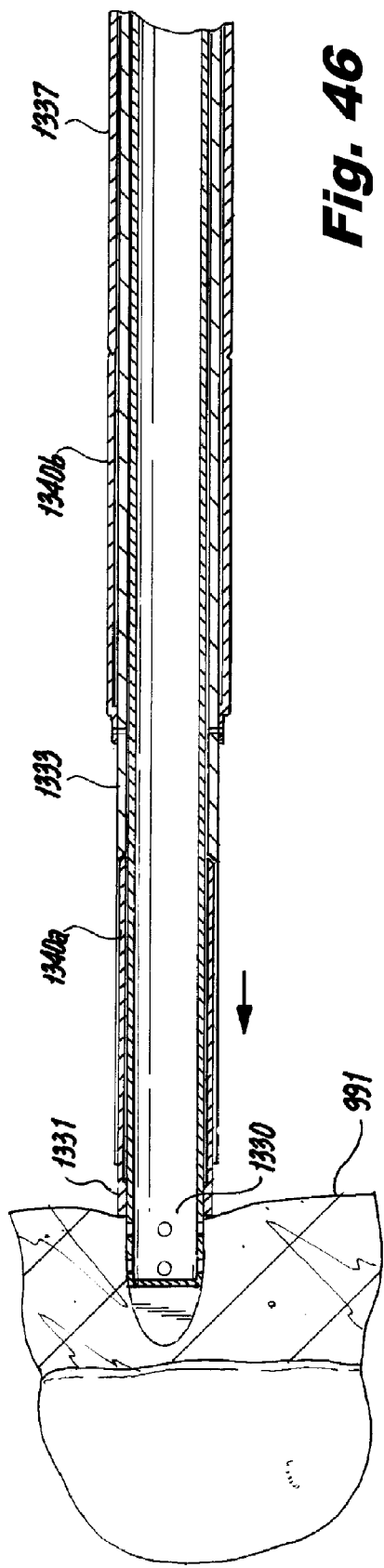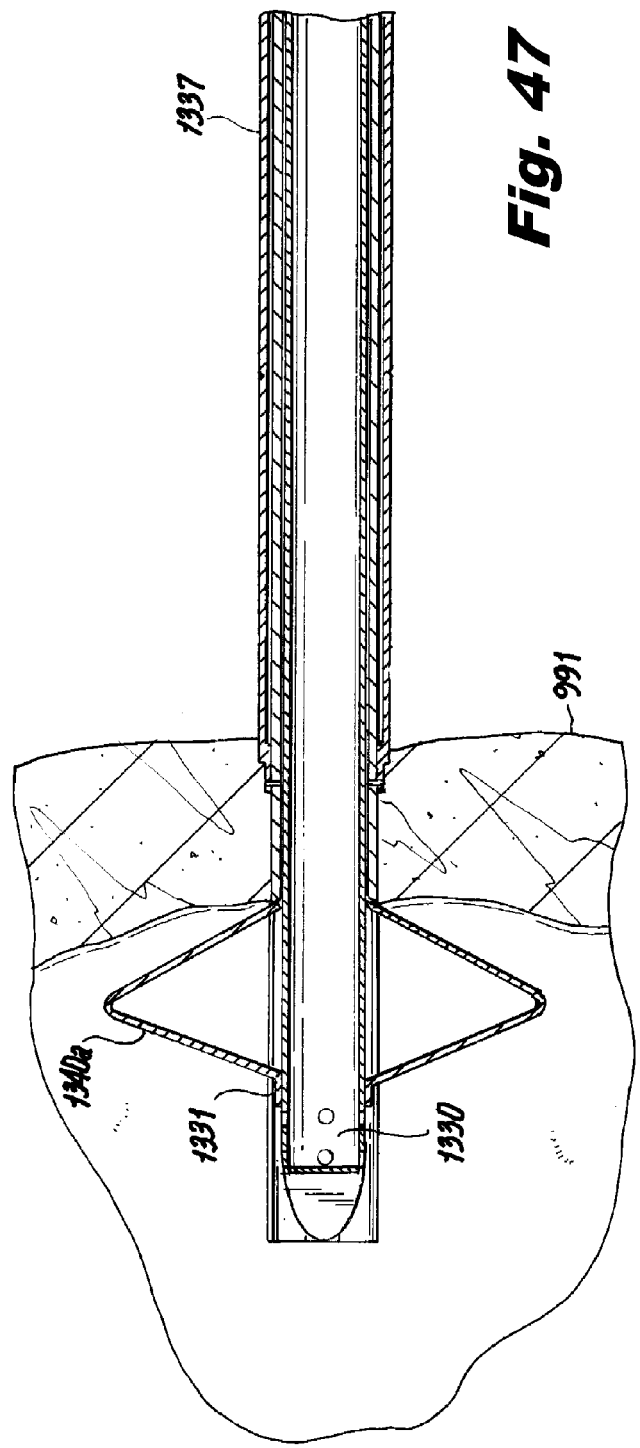

SURGICAL INSTRUMENTS FOR LAPAROSCOPIC ASPIRATION AND RETRACTION

CROSS-REFERENCE TO RELATED APPLICATIONS

This application claims the benefit of priority to U.S. Patent Application Ser. No. 61/291,842, filed Dec. 31, 2009 and U.S. Patent Application Ser. No. 61/323,359, filed Apr. 13, 2010, which are incorporated herein by reference, in their entireties.

FIELD OF THE INVENTION

The present invention relates to surgical procedures. Particularly, the present invention is directed to devices for laparoscopic surgical procedures, and more particularly to devices for use in single-incision laparoscopic surgical (SILS) procedures. The subject surgical devices are deployed, in accordance with one aspect, from within the lumen of a needle or from an outer surface of a needle. Such devices are sometimes termed "needlescopic." U.S. Patent Publications Numbers US 2010/0016884, US 2009/0259225, US 2008/0086166, US 2007/0282170, US 2007/0250112, US 2007/0213767, US 2007/0213766, and US 2007/0213595, each of which is incorporated herein by reference, in its entirety, describe devices related to the devices described herein. The devices described therein, and aspects thereof, including configuration of control mechanisms, material selection, fabrication techniques, as well as other aspects, can be applied to the devices described herein, with advantageous effect.

DESCRIPTION OF RELATED ART

Gallbladder surgery has been revolutionized in recent years, changing from an open incisional surgery to, currently, almost a purely laparoscopic procedure, also known as a minimally invasive surgery. Conventional minimally invasive surgeries for cholecystectomy involve the use of four trocars (access devices). In general, one trocar is inserted in the umbilicus, through which an endoscope is inserted, with two trocars being inserted on the right side of the abdomen for retraction and mobilizing the gallbladder, in order to identify the important structures. The fourth trocar is typically inserted in the midline above the umbilicus.

The aforementioned method has become the standard approach and has withstood twenty years of changes in surgical skill sets, in various groups of surgeons. Relatively recently, even newer and advantageous techniques for cholecystectomy have been developed that involve only a single trocar or "port", called SILS (single incision laparoscopic surgery). The prediction is that nearly twenty to forty percent of all gallbladder surgeries will be performed in this manner in the next five to ten years. This technology involves inserting a single port inserted through the umbilicus, with all the instruments going into the abdominal cavity through the single port. Mobilizing and retracting the gallbladder is challenging with this technology, especially if the gallbladder is distended due to inflammation.

There are techniques available at present for anchoring the fundus of the gallbladder with sutures during SILS procedures, although such techniques are very cumbersome and difficult, especially with an inflamed gallbladder.

Applicants recognize that aspirated, emptied gallbladders are preferable if using SILS technology for cholecystectomy, thus changing what was a tense, full sac, into a malleable structure permitting instruments to grasp the wall of the gallbladder. Applicants further recognize that simply aspirating with a needle alone, and not sealing the opening caused thereby, will cause spillage of left-over materials, which is not desirable.

Accordingly, there remains a need in the art for devices that facilitate aspiration and retraction of gallbladder in laparoscopic procedures that prevent spillage of gallbladder contents. The present invention provides a solution for these needs.

SUMMARY

In one aspect, a surgical instrument for laparoscopic procedures is provided, which is adapted and configured to aspirate and retract a hollow organ. The surgical instrument includes a needle body, an anchor, deployable with respect to the needle body, adapted and configured for engaging and retracting the hollow organ, and an aperture provided in connection with the needle body, adapted and configured for permitting aspiration of contents of the hollow organ.

The hollow organ can be a gallbladder. The anchor can be held within, and deployable from, a lumen of the needle body. The anchor can be held on, and deployable from, an outside surface of the needle body.

The anchor can be a deployable cage structure. The cage structure can be spring-biased such that the cage structure is deployed by tension provided in a spring when the cage structure extends beyond the needle body by a predetermined distance. The cage structure can include one or more barbs configured to extend from the cage structure when the cage structure is in a deployed configuration. Such one or more barbs can be distally directed to facilitate reinsertion of the cage structure into the lumen of the needle body. Alternatively, such one or more barbs can be proximally directed to facilitate engagement of the barbs with the inner wall of the hollow organ. The cage can be configured so that the barbs move into a position coplanar with surrounding portions of the cage, to facilitate reinsertion of the cage into the lumen of the needle body.

The cage structure can be provided with at least one fenestration to facilitate bending manipulation of the cage.

The cage structure can be provided with a plurality of legs, symmetrically arranged about a longitudinal axis of the surgical instrument. The number of legs can be any or two, three, four, five, six, seven, eight or nine, for example. However, greater or fewer legs, such as one or ten and so on, can be provided.

The cage structure can include a plurality of nested cages to permit flexibility of the cage while maintaining strength sufficient to reliably retract the hollow organ.

In accordance with another aspect of the invention, the anchor can be a deployable wire structure.

Alternatively, the anchor an inflatable structure. The anchor can be adapted and configured to be inflatable by one or more of a liquid and a gas.

The anchor can include a distal anchor portion and a proximal anchor portion, adapted and configured to engage inner and outer surfaces of the hollow organ, respectively. The distal anchor portion and the proximal anchor portion can be longitudinally spaced apart by a distance sufficient to permit engagement of a wall of the hollow organ. If desired, the distal anchor portion and the proximal anchor portion can be rotationally offset from one another by about 90 degrees, with respect to a longitudinal axis of the surgical instrument. Alternatively, the distal anchor portion and the proximal anchor portion can be substantially parallel with one another, with respect to a longitudinal axis of the surgical instrument.

The distal anchor portion and the proximal anchor portion can be of substantially the same configuration. Alternatively, the distal anchor portion and the proximal anchor portion can be of dissimilar configurations, such as in structure, number of elements, size, material, or in other aspects thereof.

In accordance with the invention, the needle body can include a sharpened distal tip. A deployable tip protector can further be provided to inhibit unintentional injury by a sharpened distal tip of the needle body. The deployable tip protector can be a translatable sheath adapted and configured to be deployed over the sharpened distal tip of the needle body. Alternatively, the deployable tip protector can be a translatable plug adapted and configured to be deployed from within a lumen of the needle body. The plug can be adapted and configured to extend distally beyond the sharpened distal tip of the needle body, to inhibit piercing of a structure by the needle body, when in a deployed position. The plug can be formed from a polymeric material.

In accordance with the invention, an aperture can be provided at the distal end of the body. Alternatively, one or more apertures can be provided in a distal end portion of a sidewall of the body.

The anchor can be formed at least in part from one of a shape-memory alloy and a stainless steel. Alternatively, resilient polymeric materials of sufficient strength, flexibility and durability can be used. In accordance with the invention, the anchor can be formed at least in part by laser cutting.

The needle body can be any length necessary. In accordance with one aspect, the length is about 20 centimeters. An outer diameter of the needle body can be any size necessary. In accordance with one aspect, the diameter is about 2 mm.

The anchor can be configured such that, in a deployed conformation, a width, measured transverse to a longitudinal axis thereof, is a maximum of about eight times that of a width in a collapsed conformation, measured transverse to the longitudinal axis thereof.

The needle body can be provided with a sharpened end surface angled at about 35 degrees with respect to the longitudinal axis of the needle body.

A handle can be provided in connection with the subject instruments, to facilitate manipulation thereof.

In accordance with a further aspect of the invention, a method of retracting a hollow organ is provided, comprising the steps of inserting a body through an abdominal wall of a patient, inserting the body through a wall of the hollow organ, aspirating contents from the hollow organ, deploying a first anchor portion within the hollow organ, to engage an inner surface of the hollow organ, and retracting the hollow organ.

In accordance with the invention, the method can further include the step of deploying a second anchor portion outside the hollow organ to engage an outer surface of the hollow organ.

In accordance with still another aspect of the invention, a surgical instrument for laparoscopic procedures is provided, which is adapted and configured to aspirate and retract a gallbladder, the instrument having means for aspirating contents from a gallbladder, and means for engaging and retracting the gallbladder.

In accordance with still a further aspect of the invention, a surgical instrument can be manufactured by a process comprising the steps of providing a tubular needle with a lumen extending therethrough, machining a deployable anchor, and inserting the deployable anchor, in a radially collapsed conformation, into the tubular needle. The anchor can be formed from a flat stainless steel stock material. The step of machining can be performed by electrical discharge machining or laser machining, for example.

It is to be understood that both the foregoing general description and the following detailed description are exemplary and are not intended to be limiting.

BRIEF DESCRIPTION OF THE DRAWINGS

The accompanying drawings, which are incorporated in and constitute part of this specification, are included to illustrate and provide a further understanding of the devices and related methods of the invention. Together with the description, the drawings serve to explain the principles of the invention, wherein:

FIGS. 1-14 show various views of a surgical aspirator-retractor in accordance with the present invention, having a deployable anchor element thereof, in a cage having a rosette configuration;

FIG. 1 is an isometric view of a first representative embodiment of a surgical aspirator-retractor in accordance with the present invention, with a distal anchor portion thereof shown in a collapsed condition;

FIG. 2 is an isometric view of the surgical aspirator-retractor of claim 1, with a distal anchor portion thereof shown in an expanded condition;

FIG. 3 is a side view of the surgical aspirator-retractor of FIG. 1 in accordance with the present invention, with a distal anchor portion thereof shown in a collapsed condition;

FIG. 4 is a detailed isometric view of the distal anchor portion of the surgical aspirator-retractor of FIG. 1, shown in a collapsed condition;

FIG. 5 is a detailed isometric view of the distal anchor portion of the surgical aspirator-retractor of FIG. 1, shown in an expanded condition;

FIG. 6 is a detailed isometric view of the distal anchor portion of the surgical aspirator-retractor similar in all respects to the embodiment of FIG. 1, but with a solid tip and apertures for aspiration on a side surface thereof, shown in a collapsed condition;

FIG. 7 is a detailed isometric view of the distal anchor portion of the surgical aspirator-retractor of FIG. 6, shown in an expanded condition;

FIG. 8 is a proximal isometric view of the surgical aspirator-retractor of FIG. 1;

FIG. 9 is a proximal end view of the surgical aspirator-retractor of FIG. 1;

FIG. 10 is a distal end view of the surgical aspirator-retractor of FIG. 1;

FIGS. 11-14 illustrate use of the surgical aspirator-retractor of FIG. 1, in piercing, aspirating contents of and retracting a gallbladder, respectively;

FIGS. 15-22 show various views of a further embodiment of a surgical aspirator-retractor in accordance with the present invention, having a hook-shaped distal anchor element;

FIG. 15 is a distal isometric view of a further embodiment of a surgical aspirator-retractor in accordance with the invention, shown with a distal anchor portion thereof in a retracted condition;

FIG. 16 is a distal isometric view of the surgical aspirator-retractor of FIG. 15, shown with a distal anchor portion thereof in a deployed condition;

FIG. 17 is a side view of the surgical aspirator-retractor of FIG. 15, shown with a distal anchor portion thereof in a deployed condition;

FIG. 18 is a detail isometric view of a distal anchor portion of the surgical aspirator-retractor of FIG. 15;

FIGS. 19-22 illustrate use of the surgical aspirator-retractor of FIG. 15, in piercing, aspirating contents of and retracting a gallbladder, respectively;

FIGS. 23-31 show various views an additional embodiment of a surgical aspirator-retractor in accordance with the present invention, having a deployable cage anchor;

FIG. 23 is an isometric view of a surgical aspirator-retractor, having a deployable cage stowed within a lumen of a needle body;

FIG. 24 is a detail isometric view illustrating the deployable cage of the surgical aspirator-retractor of FIG. 23, stowed within the lumen of a needle body;

FIG. 25 is a detail isometric view illustrating the deployable cage of the surgical aspirator-retractor of FIG. 23, partially deployed from the lumen of the needle body;

FIG. 26 is a detail isometric view illustrating the deployable cage of the surgical aspirator-retractor of FIG. 23, fully deployed from the lumen of the needle body;

FIG. 27 is a detail cross-sectional view illustrating an example deployment mechanism for the cage of the surgical aspirator-retractor of FIG. 23;

FIG. 28 is a detail isometric view illustrating a barb provided on the deployable cage of the surgical aspirator-retractor of FIG. 23;

FIG. 29 is a detail isometric view illustrating a distal end portion of the deployable cage of the surgical aspirator-retractor of FIG. 23;

FIG. 30 is an isometric view of a distal anchor portion of a surgical aspirator-retractor in a deployable cage configuration, which is similar in many respects to the embodiment of FIG. 23, but with a plurality of nested layers and additional fenestrations to facilitate a change in conformation thereof;

FIG. 31 is a detail isometric view of the distal anchor portion of the surgical aspirator-retractor of FIG. 30;

FIGS. 32-34 show various views of still another embodiment of a surgical aspirator-retractor in accordance with the present invention having a deployable cage formed by outwardly expanding ribbons of material;

FIG. 32 is a distal isometric detail view of a surgical aspirator-retractor, with a needle tip portion covered by a sheath to inhibit unintentional damage to an anatomical structure;

FIG. 33 is a distal isometric detail view of the surgical aspirator-retractor of FIG. 32, with a needle tip portion exposed by the sheath;

FIG. 34 is a distal isometric detail view of the surgical aspirator-retractor of FIG. 32, shown in an expanded conformation;

FIGS. 35-36 show various views of a further embodiment of a surgical aspirator-retractor in accordance with the present invention having distal deployable anchor as a deployable cage, formed by axially offset pairs of outwardly expanding anchor portions formed of ribbons of material, for engaging inner and outer wall surfaces, respectively, of a hollow organ;

FIG. 35 is an isometric view of the surgical aspirator-retractor, showing the anchor portions in a deployed conformation;

FIG. 36 is an exploded view of the surgical aspirator-retractor;

FIGS. 43-48 show various views of still a further embodiment of a surgical aspirator-retractor in accordance with the present invention having axially offset pairs of outwardly expanding anchor portions formed of ribbons of material, for engaging inner and outer wall surfaces of a hollow organ, respectively;

FIG. 43 is an isometric view of a distal end portion of the surgical aspirator-retractor in accordance with the invention, shown with the anchor portion in a collapsed configuration;

FIG. 44 is an exploded view of the surgical aspirator-retractor of FIG. 43;

FIG. 45 is an isometric view of a distal end portion of the surgical aspirator-retractor of FIG. 43, shown with the anchor portion in a deployed configuration;

FIG. 46-48 are side views illustrating insertion and deployment of the of the surgical aspirator-retractor of FIG. 43 within and outside of a hollow organ, and subsequent engagement thereof;

DETAILED DESCRIPTION

Figure 3:
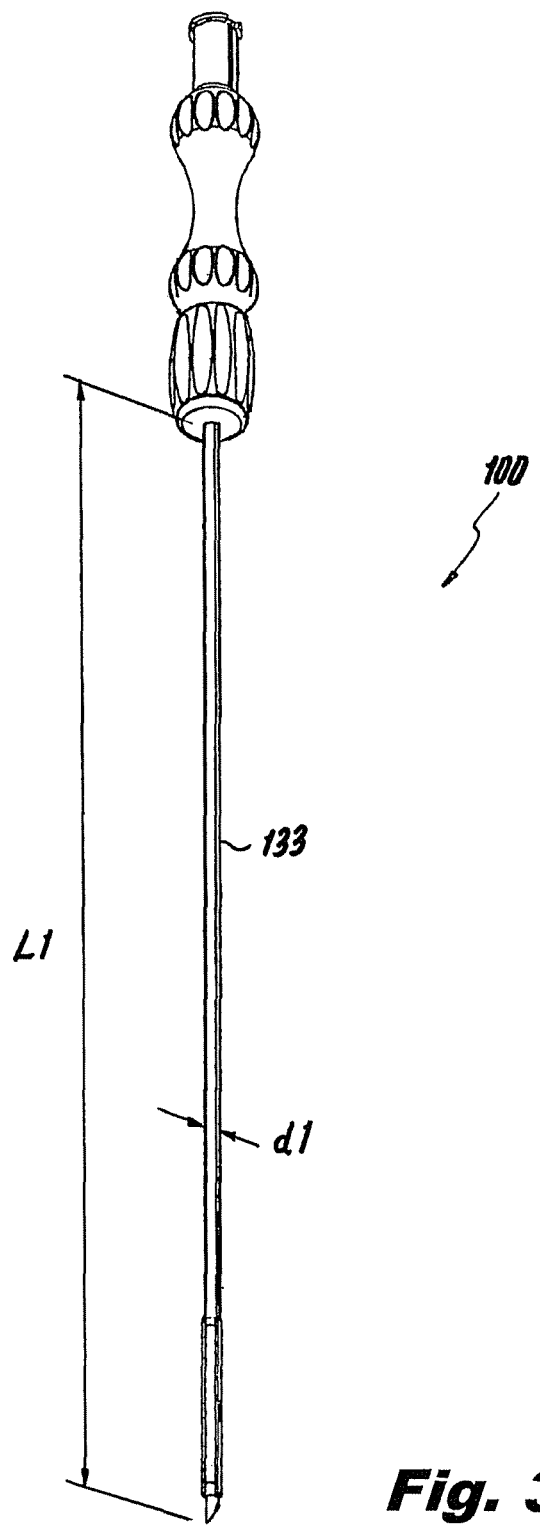

Reference will now be made in detail to the present preferred embodiments of the invention, examples of which are illustrated in the accompanying drawings.

In accordance with one aspect of the invention, a surgical aspirator-retractor is provided having the capacity to aspirate and seal a hole formed thereby, as well as retract the gallbladder. In accordance with one aspect, a needle of less than 2.5 mm is introduced into the abdominal wall with a sharp tip which can pierce the skin. The same needle tip is able to pierce the fluid-filled gallbladder wall. The opposite end to the needle tip can be provided with a hub to attach a syringe or suction device to help to aspirate the contents of the gallbladder. Once the gallbladder is emptied of its contents, the surgical aspirator-retractor's anchor or fixation mechanism can be deployed.

In accordance with the invention, the distal anchor or fixation mechanism can include, for example, multiple curved wires coming out of the sharp end of the needle, multiple curved wires coming out of the shaft near the needle tip, an outer shaft over the needle having a shape-memory alloy wire attached to two ends and when pushed down, the wire assumes the shape of a rosette. Depending on the precise implementation, the needle tip can be split at the end and when retracted backwards can become the shape of a star. If desired, a separate instrument can be provided having a compressed hook, introduced at the proximal end of a needle body. When the separate instrument is inserted through and beyond a distal end of the needle body, it is deployed, and the hook engages the inside of the gallbladder wall.

Depending on the precise embodiment, once this distal anchor portion is deployed, the whole instrument is withdrawn until the sharp tip of the anchor engages and fixes to the inside of the gallbladder wall firmly. Optionally, a second anchor portion can be provided to engage the outer surface of the wall of the gallbladder to facilitate a secure grasp. The gallbladder can then be retracted or mobilized in any direction without any spillage. Once the gallbladder dissection from the liver is complete, the anchor mechanism is either retracted into the instrument or otherwise straightened, thus releasing its attachment from the gallbladder wall. The instrument will then be withdrawn from the gallbladder wall.

It should be noted that although the devices of the present invention are advantageous for cholecystectomy procedures, they can advantageously be applied to aspirate, retract and/or stabilize other hollow organs, such as the stomach or urinary bladder, for example. Further, devices in accordance with the invention can be used to manipulate other tissues including organs, in addition to those that are substantially hollow.

Devices in accordance with the invention advantageously help empty the contents from the organ with which it is being used, such as the gallbladder, without spillage, and facilitate easy grasping of the wall of the thereof because of loss of distensability of the organ wall is reduced. The subject devices also permit easy removal of the gallbladder from the abdominal cavity through the umbilical port due to the collapsed state of the organ. Further, advantageously, the small size of the subject instruments minimize or eliminate scarring.

For the purposes of explanation and illustration, and not limitation, in accordance with the invention, an exemplary embodiment of a surgical aspirator-retractor 100 is illustrated in FIGS. 1-14. In accordance with this example, the surgical aspirator-retractor includes an inner needle having a diameter, for example 1.5 mm, and a needle body 130 having diameter d1, for example about 2 mm, with a length L1, for example about 200 mm.

As illustrated in FIGS. 11-14, which illustrate use of the surgical aspirator-retractor of FIG. 1, in piercing, aspirating contents of and retracting a gallbladder, respectively, the aspirator-retractor 100 can be positioned directly over the gallbladder 991 then inserted directly through the skin of the abdominal wall 990, into the gallbladder 991, by virtue of a sharpened distal tip 131. A suction source can be hooked up to a fitting 115, such as a Luer fitting provided on the body 110, and the gallbladder is aspirated of its contents 993, such as bile, from the lumen 995 thereof, via a distal end aspiration aperture 135 therein. The thumb wheel 120 can then be advanced to deploy the anchor 140, which in the illustrated embodiment is in the form of a cage with hooks or barbs 141 to engage or imbed into the gallbladder 991, for retention thereof. The surgical aspirator-retractor 100 is then pulled up setting the tips of the cage into the gallbladder internally. The surgical aspirator-retractor 100 can then be pulled up and the gallbladder is raised to the desired position. The position locking mechanism 150 is placed against the skin and locked, thereby suspending the gallbladder in the body cavity allowing work to be performed on it and around it without having to reposition the gallbladder continually.

Figure 4:
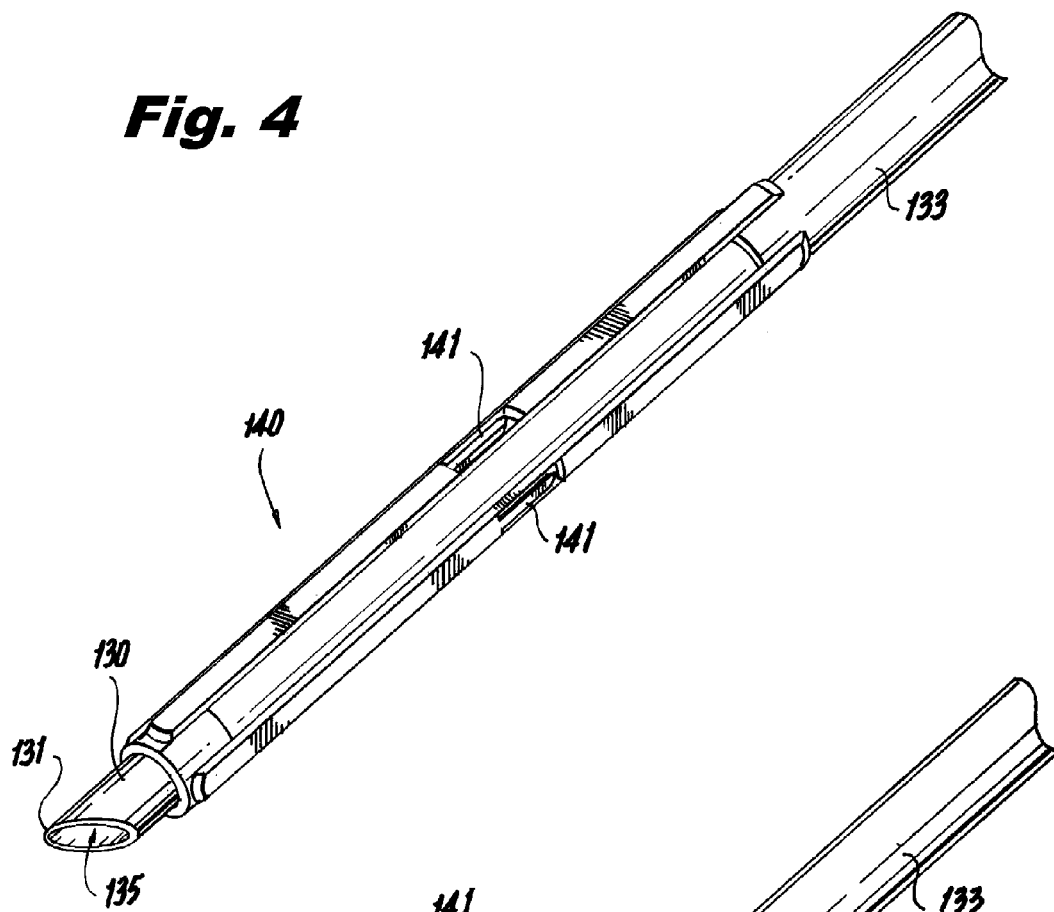
Figure 5:
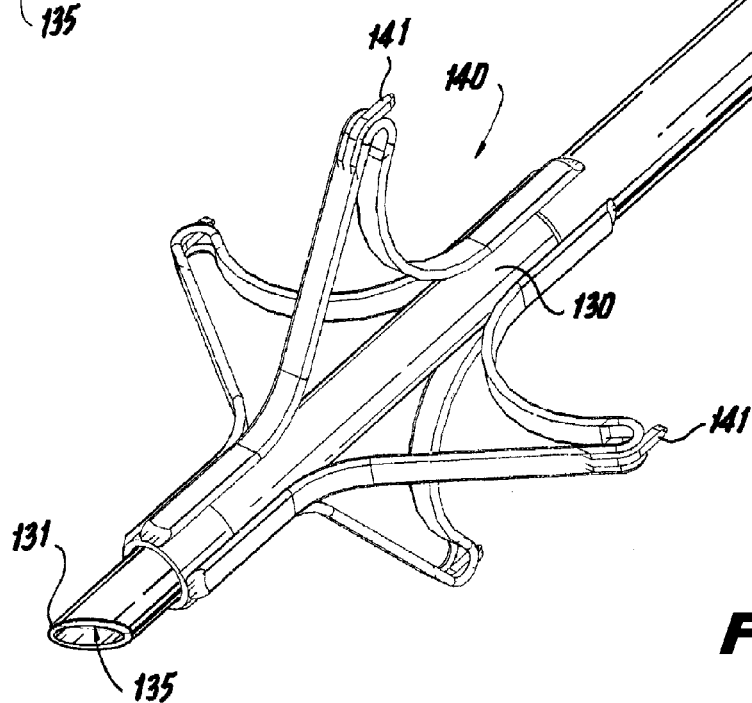

As best seen in the detail views of FIGS. 4 and 5, an outer shaft 133 is provided concentrically outside of the needle body 130, and is attached to the proximal end of the anchor 140, while the distal end of the anchor 140 is attached to the needle body. Such attachment can be achieved by integral forming process, welding, crimping, mechanical fasteners, adhesives or another suitable technique, if desired.

Figure 6:
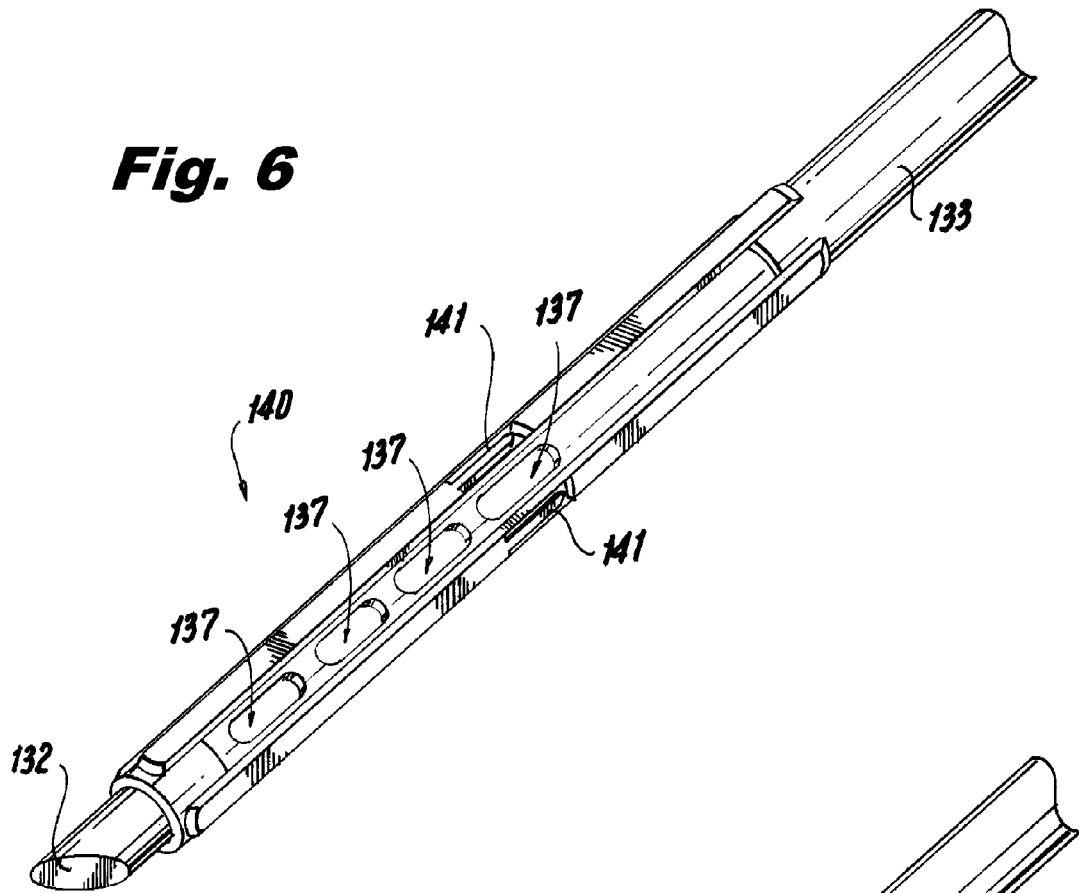
Figure 7:
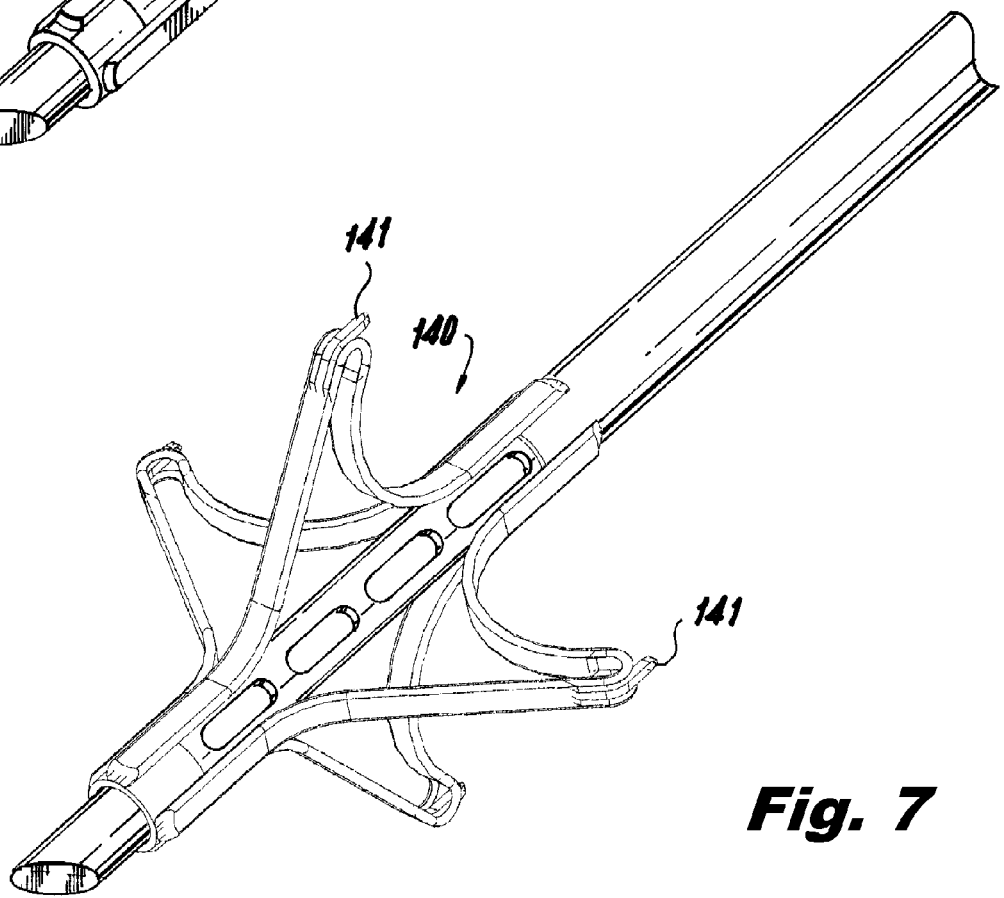
Figure 8:
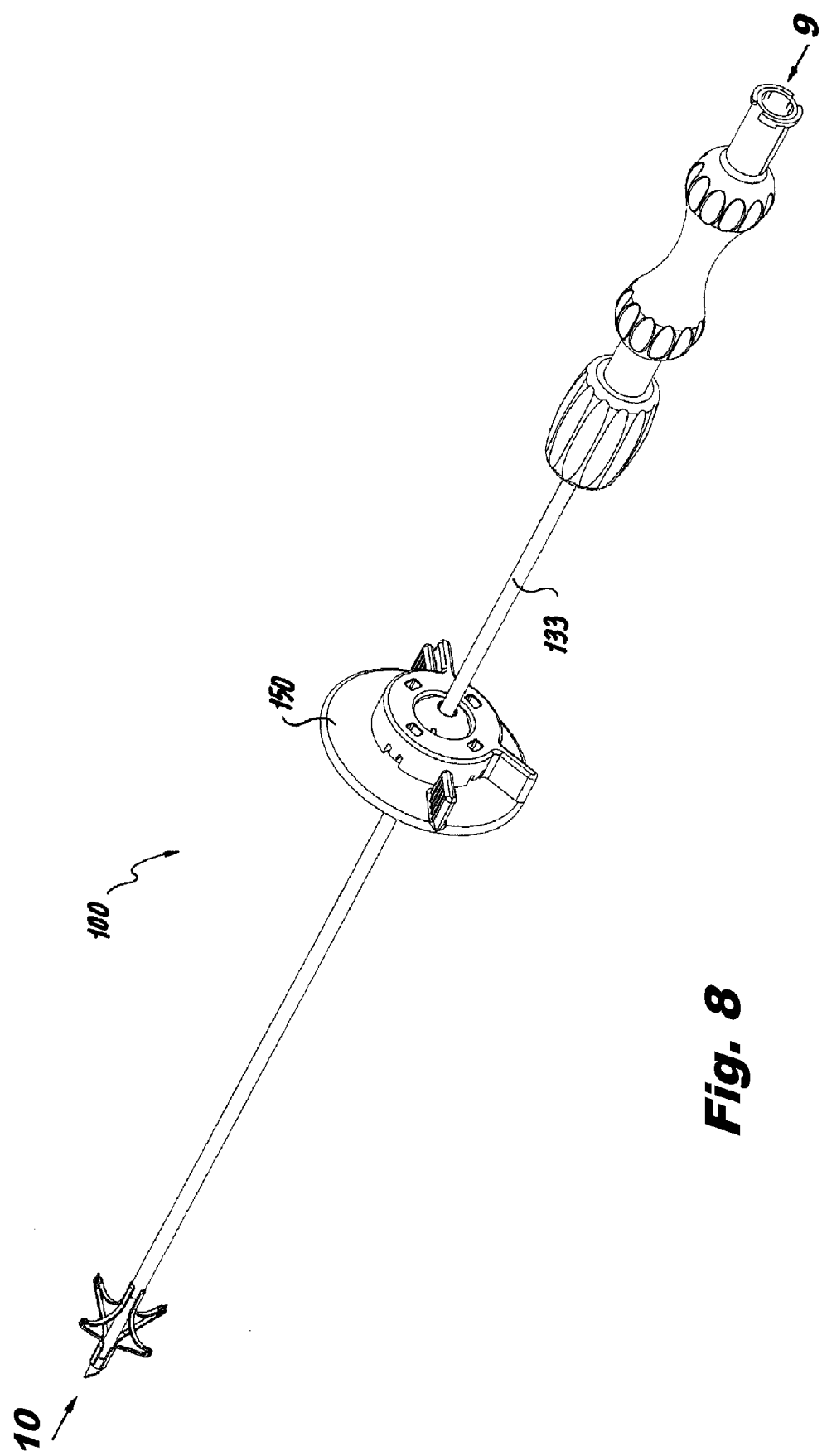
Figure 9:
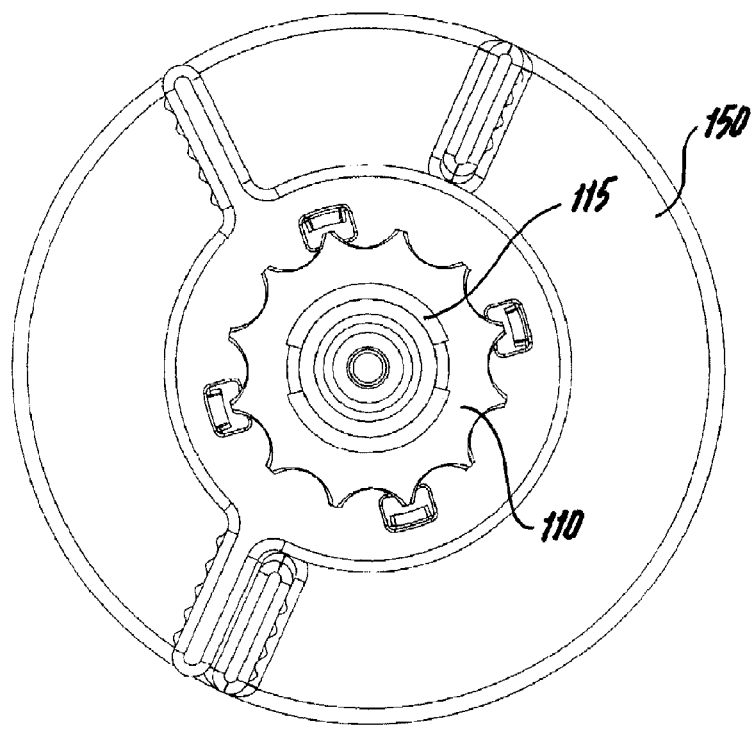
Figure 10:
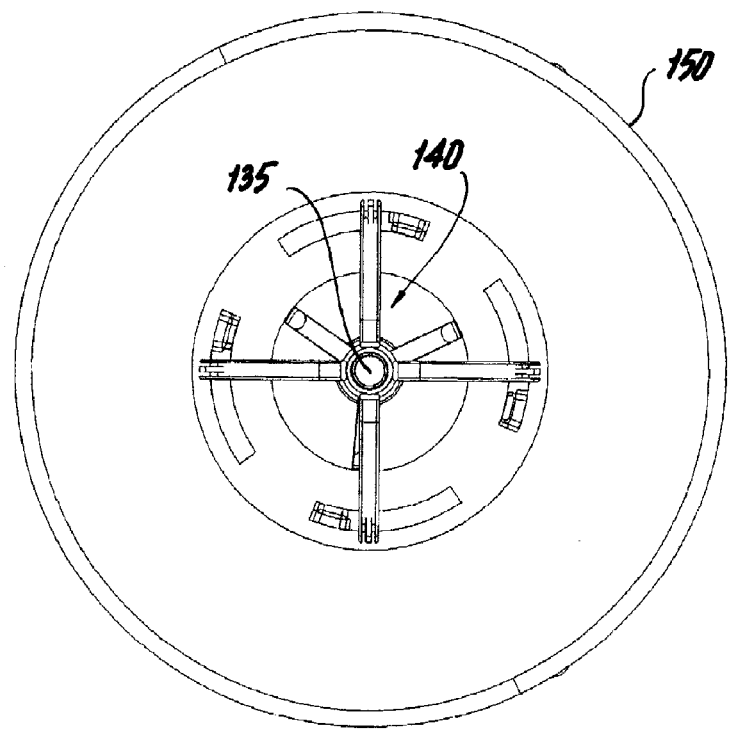
Figure 11:
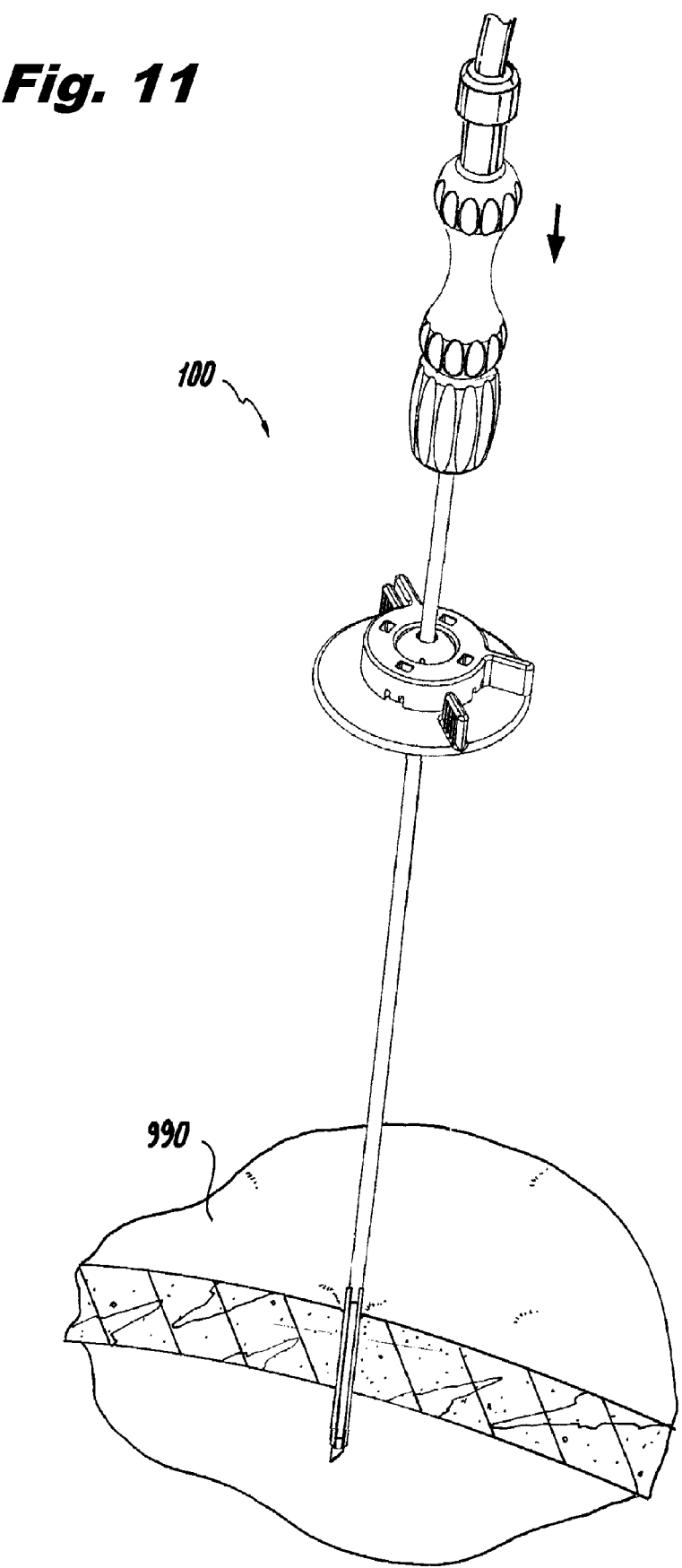
Figure 12:
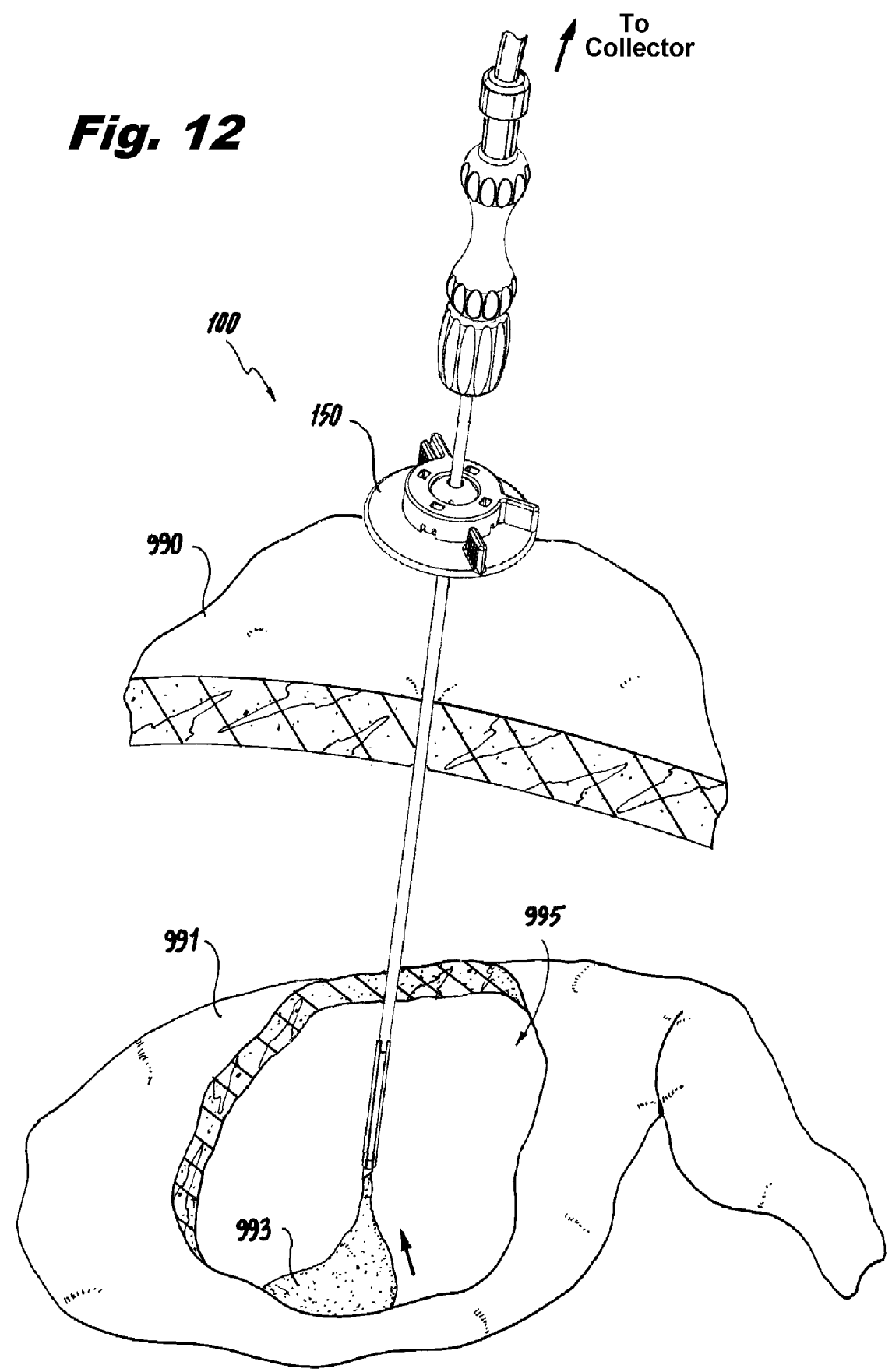
Figure 13:
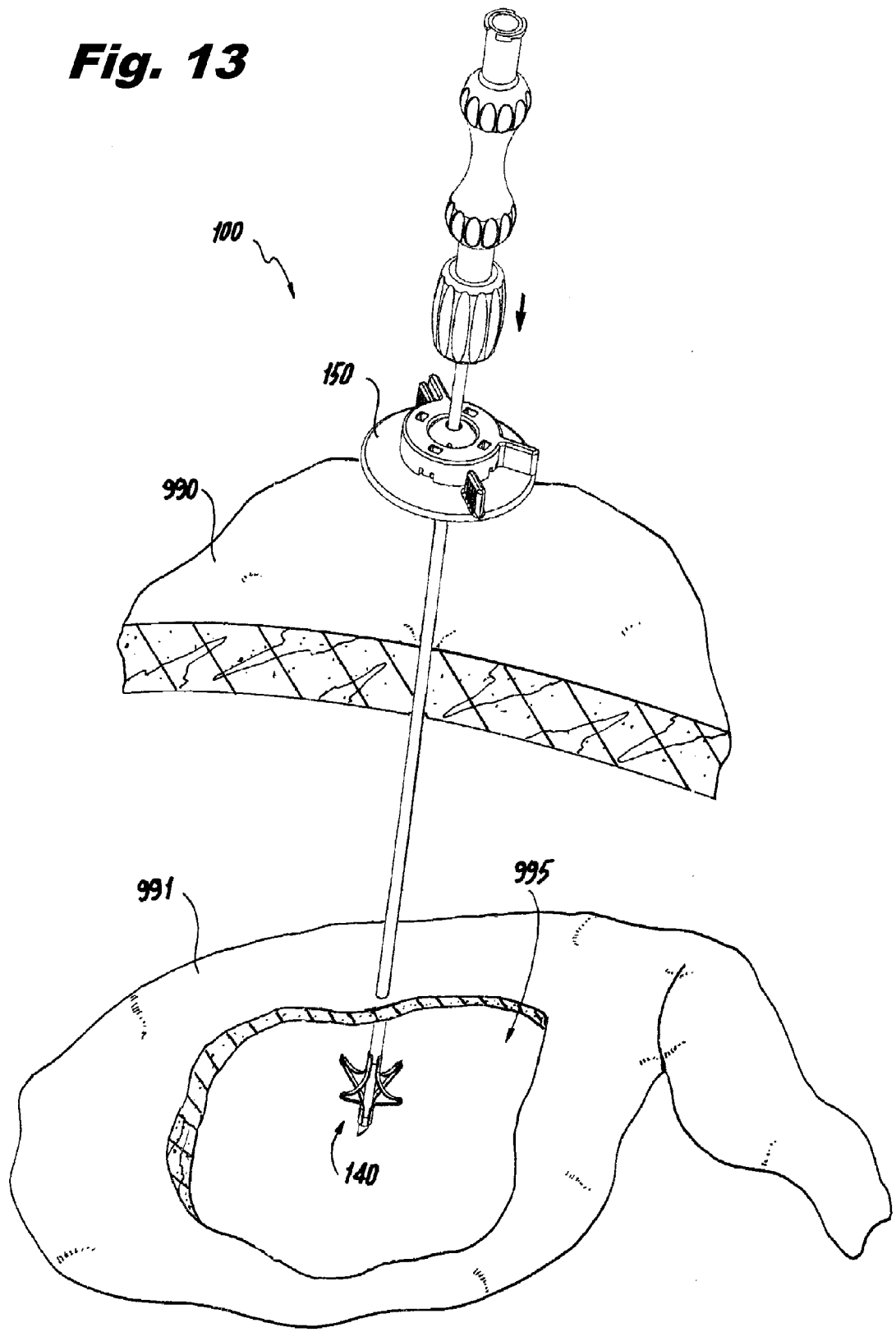
Figure 14:
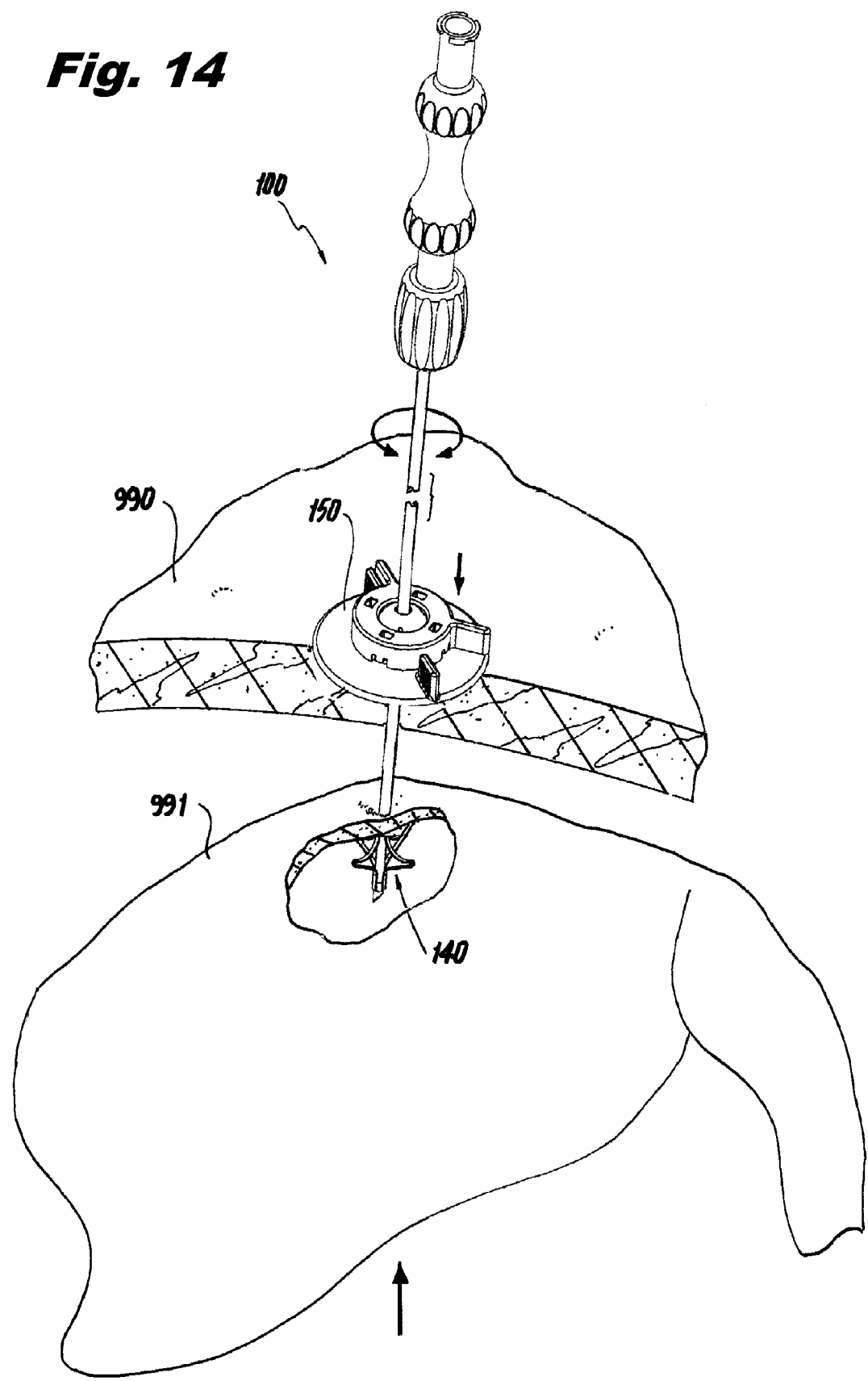
Figure 17:
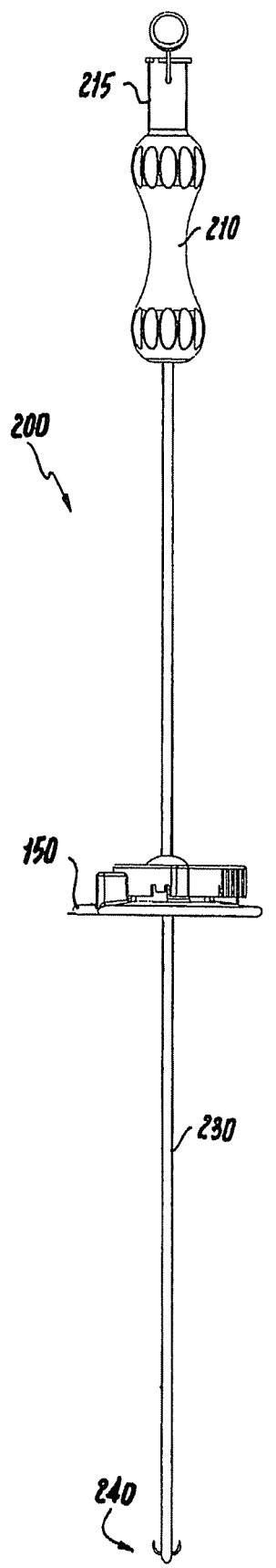
Figure 18:
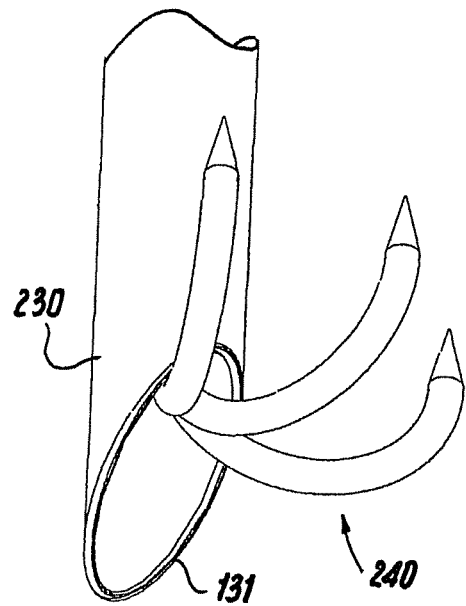

FIGS. 6 and 7 are is an isometric detail views of the distal anchor portion 140 of the surgical aspirator-retractor 100, but with a solid tip 132 and apertures 137 for aspiration on a side surface thereof, shown in a collapsed condition and a deployed condition, respectively.

In accordance with a further exemplary embodiment, as illustrated for example, in FIGS. 15-22, a surgical aspirator-retractor 200 is provided with a needle body 230, a distal anchor 240, a handle 210, a proximal fitting 215 and a position locking mechanism 150. The needle body 230 can have, in accordance with one example embodiment, a diameter of about 1.5 mm and a length of between about 150 mm and 200 mm.

Figure 21:
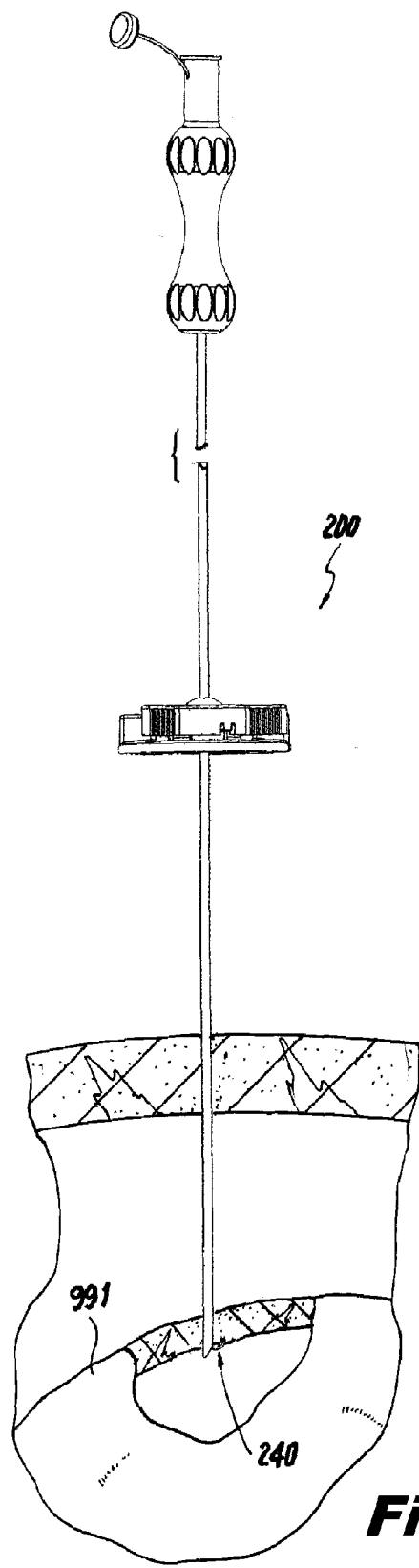
Figure 22:
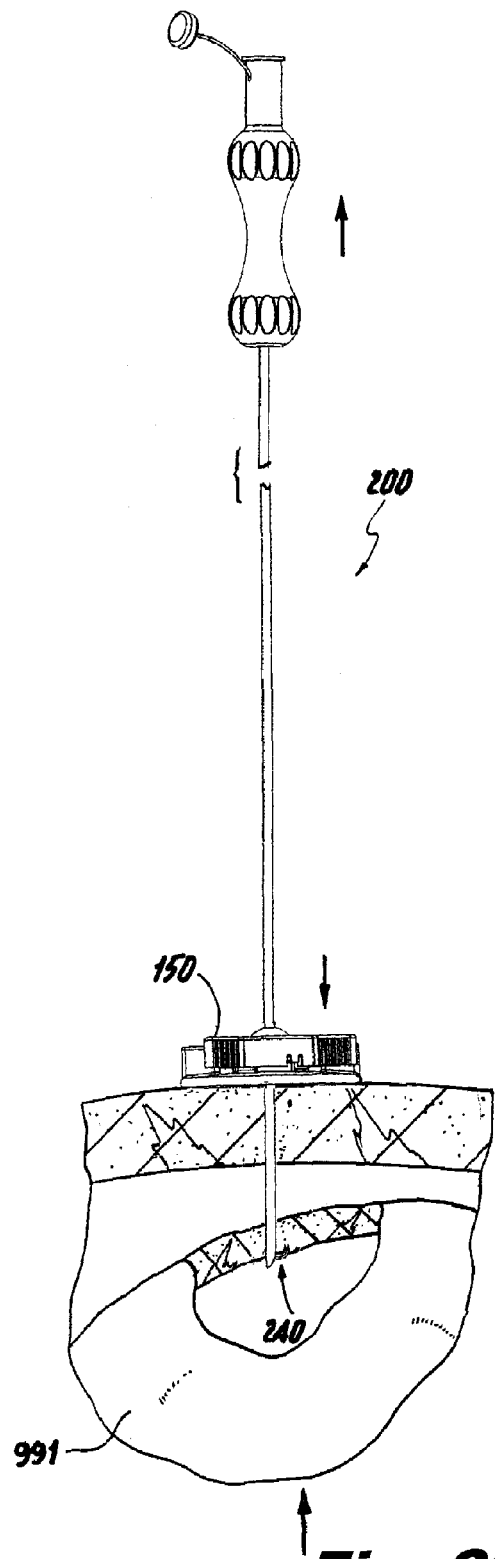
Figure 25:
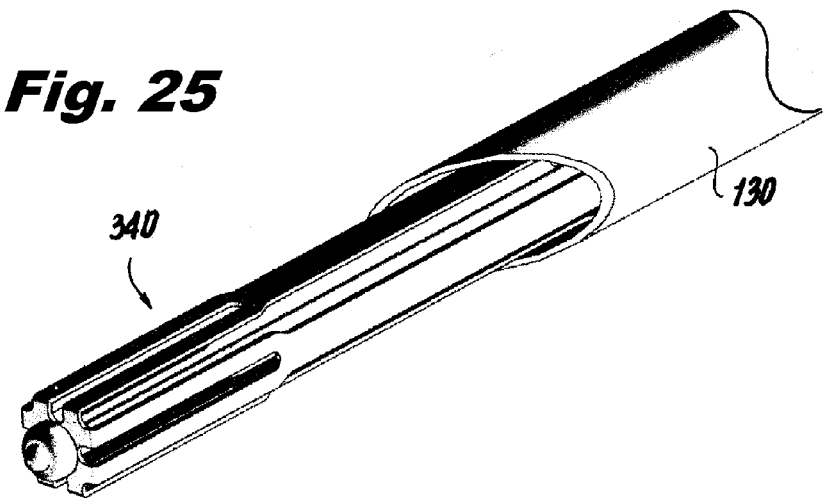
Figure 26:
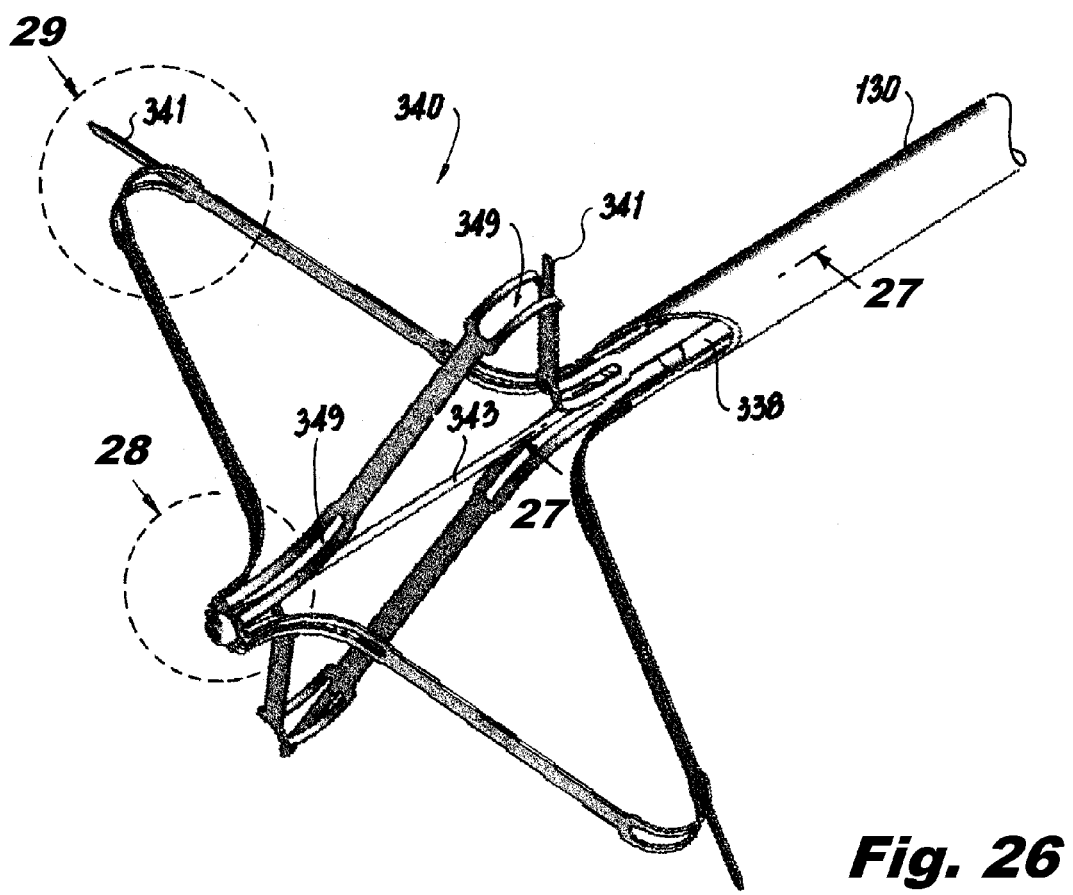

As best seen in FIGS. 19-22, which illustrate use of the surgical aspirator-retractor of FIG. 15, in piercing, aspirating contents of and retracting a gallbladder, respectively, as with the above-described embodiment, the aspirator-retractor 200 can be positioned over the gallbladder 991, and then inserted directly through the abdominal wall 990, into the lumen 995 of the gallbladder 991. Suction can then be hooked up to the luer fitting 215 on the end thereof, and the gallbladder 991 is aspirated of its contents 993, such as bile. Suction can then be turned off and the anchor 240 advanced, as shown in FIG. 21, to expose a single or multiple needle tips (e.g., similar to a grappling hook). As shown in FIG. 22, the surgical aspirator-retractor 200 is then pulled up setting the needles into the inner surface of the wall of the gallbladder 991. Then, the surgical aspirator-retractor 200 is pulled up and the gallbladder is raised to the desired position. The position locking mechanism 150 is placed against the skin and locked, thereby suspending the gallbladder in the body cavity allowing work to be preformed on it and around it without having to continually reposition the gallbladder 991.

FIGS. 23-31 show various views an additional embodiment of a surgical aspirator-retractor in accordance with the present invention, having a deployable cage-shaped anchor 340.

By way of example, the needle body 130 is provided as a hollow needle. In accordance with one aspect, the diameter of the needle body 130 can be about 2.1 mm. In use, the needle body is inserted through the abdomen under internal observation. The needle body 130 is inserted into the gallbladder 991 and fluids are aspirated through the needle body 130. A shaft 340, which may be formed from a tubular material, and being internal to the needle body 130, is advanced distally to deploy the expandable cage-shaped anchor 340, which is affixed to the front of the tube 338. A shaft 343 runs through a lumen of the tube 338, and is attached to the distal portion of the anchor cage 340. As best seen in FIG. 27, a spring 345 is provided and is secured to the shaft 343, thus spring loading the anchor cage 340, under tension applied thereto. When the anchor cage 340 is advanced beyond the needle body 130, the tension of the spring 345 causes the cage to expand up to a stop. Bending of the anchor cage 340 exposes grip fingers or barbs 341 that secure the inside of the gall bladder 991.

In use, the internal components are typically recessed inside the 2.1 mm hollow needle body 130. The needle body 130 is then inserted through the abdomen and then into the gallbladder 991. Fenestrations 349 facilitate achieving the desired structural properties of the anchor cage 340, and also permit fluids to be aspirated past the distal tip of the anchor cage 340. Once the gallbladder 991 is aspirated, the anchor cage 340 is advanced through the needle body 130, and into the lumen 995 of the gallbladder 991. In accordance with one aspect, the anchor cage 340 expands outwardly, to a maximum width of about 16 mm. In the illustrated embodiment, the barbs 341 face distally, so that there are no edges to catch on the needle body 130, when the cage 340 is drawn back into the needle body 130.

After insertion within the lumen 995 of the gallbladder 991 and deployment of the anchor 340, the aspirator-retractor can be manipulated such as by rotation or axial translation, to facilitate access to the gallbladder 991. Once removed, the gallbladder 991 is placed in a bag, for example, and the anchor cage 340 is retracted to release the gallbladder 991 from the aspirator-retractor, which is then removed from the patient.

To retract the anchor cage 340, the inner drive tube 338 is retracted. The gallbladder is then stripped from the aspirator-retractor. The anchor cage 340 is then returned to its original position and the needle body 130 is removed from the abdomen.

In accordance with the invention, the anchor cage 340 is assembled by any suitable technique, to the inner tube 338, such as by welding, soldering or crimping. In accordance with the invention, the shaft 343 can be connected to the anchor cage 340 by a threaded connection, or other suitable technique.

Due to the high amount of flex and associated strain placed on the cage, material must be selected accordingly. Shape memory alloys or any suitable materials can be used. In accordance with one aspect, a high strength stainless steel alloy is used in cased of thin cross-sections, to maintain stresses below their tensile limits. In accordance with the invention, 17-7PH Condition C stainless steel with a post forming heat-treatment to condition CH900 can be utilized for this application. In accordance with the invention, such a material can have a tensile strength of approximately 250,000 psi and elongation of 3% expected, with minimal part distortion during heat-treatment. If desired, a flash electropolish and subsequent low temperature bake to prevent Hydrogen embrittlement can be used to remove heat tint during 900 degree F. open air precipitation age hardening.

Figure 30:
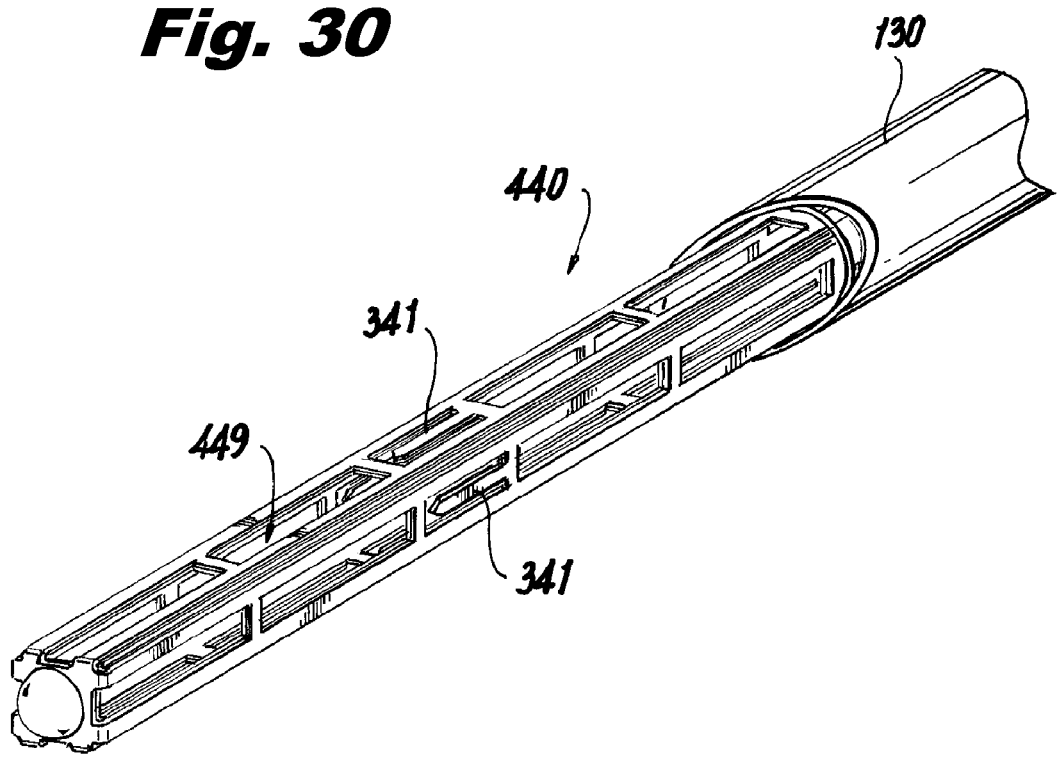
Figure 31:
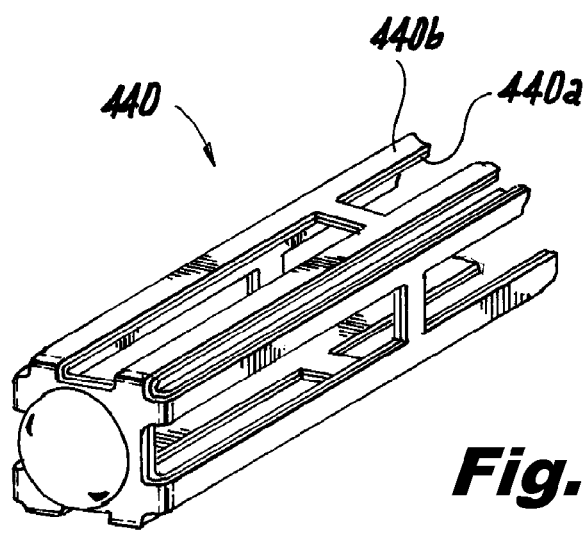

FIG. 30 is an isometric view of a distal anchor 340 of a surgical aspirator-retractor having a deployable cage configuration, which is similar in many respects to the embodiment illustrated in FIG. 23. The anchor cage 440 differs therefrom in that it includes a plurality of nested layers 440a, 440b, and additional fenestrations 449, to promote strength while facilitate a reliable change in conformation thereof in use. FIG. 31 is a detail isometric view of the distal anchor portion 440 of the surgical aspirator-retractor of FIG. 30. In accordance with one aspect of the invention, the anchor cage 340 and/or the anchor cage portions 440a, 440b can be formed from a stainless steel material having about a 0.002 inch stock thickness.

With reference to FIGS. 32-34, still another embodiment of a surgical aspirator-retractor in accordance with the present invention is illustrated, having a distal anchor 540 in a variation of the above-described deployable cage structures. The distal anchor 540 includes outwardly expanding ribbons of material 540a, 540b. A main needle body 530 is provided, axially inner to other components. A deployable tip protector 537 is also provided. As illustrated in FIG. 32, the tip protector 537 is here illustrated as a sheath which can be deployed by manipulating respective concentric tube(s), such as one provided radially outward from the main needle body 530. As best seen in FIG. 34, when a compressive force is applied distally on the ribbons 540a, 540b, they expand radially outwardly, as with other embodiments described herein, due to the configuration thereof and material selection therefor.

FIGS. 35-36 illustrate a further embodiment of a surgical aspirator-retractor in accordance with the present invention having a distal deployable anchor 640 as a deployable cage, formed by axially offset pairs of outwardly expanding anchor portions 640a, 640b, which are generally ribbon-shaped in configuration.

In accordance with the invention, the needle body 630 can be configured as desired. In accordance with one aspect of the invention, the needle body 630 has about a 2.1 mm outer diameter and 225 mm length. A safety plug 639 can be provided for the same reason as the sheath 537 of the above-described embodiment, namely to inhibit unintentional trauma to the patient when the needle body 130 is not intentionally and actively being inserted through anatomy. In the safe position illustrated in FIG. 35, a sharp tip of the needle body 630 is shielded by the plug 639, which extends distally past the tip thereof.

Conversely, to pierce a structure, the plug 639 is retracted by withdrawing the cage 640 proximally. Suction applied to a central lumen allows for aspiration of contents through the lumen, around the plug 639. Alternatively or additionally, fluid can be aspirated through the (four) fenestrations in the needle body 630 provided for the expanding anchor portions 640a, 640b. Aspirated contents can be carried through an inner tube and to the connected suction system.

Later, for deployment of the anchor portions 640a, 640b, the cage 640 is urged distally, which also results in the plug 639 being placed in the safety position. In the illustrated embodiment, tabs formed by on respective legs of the cage 640 engage respective slots in a pushing element, or expander 642 and a pusher tip 644. The expander 642 and pusher tip 644 can be welded to respective inner and outer tubes, such as actuator 646, that can be move axially relative to one another, to enable control of deployment of the cage 640.

In use, an inner tube (not illustrated) connected to the expander 642, can be advanced distally to deploy the distal grasper portions 640b, within the gallbladder. The whole aspirator-retractor can then be retracted proximally until the set of distal anchor portions 640b are engaged with an inner surface of the gallbladder wall. The outer tube 646, connected to the pusher 644 can then be advanced to open the proximal grasper portions 640a, to expand on the outside of the gallbladder, sandwiching the wall of the gallbladder therebetween.

Thus, the aspirated gallbladder is securely held by the aspirator-retractor and is able to be manipulated by the surgeon while it is dissected from connecting vessels and tissues. In accordance with one aspect, the gallbladder can then be placed in an endoscopic collection bag and both inner and outer tubes can be retracted to pull the anchor portions 640a, 640b inside of the needle body 630, to release the gallbladder. Subsequently, the aspirator-retractor can then be removed from the abdomen and discarded.

As with other embodiments set forth herein, the illustrated configuration of an aspirator-retractor can be integrated with handles described herein.

As with other embodiments described herein, the anchor portions 640a, 640b extend through respective apertures, which are formed, in this case, in the needle body 630 by a suitable technique, such as by laser cutting.

In accordance with one aspect, the anchor cage portions 640a, 640b can be formed of a 0.005 inch-thick, full hard stainless steel, or another suitable material. The Anchor cage 640 can be formed from a single or a plurality of nested layers.

Various additional alternative embodiments of aspirator-retractors in accordance with the invention are provided, as follows.

Figure 37:
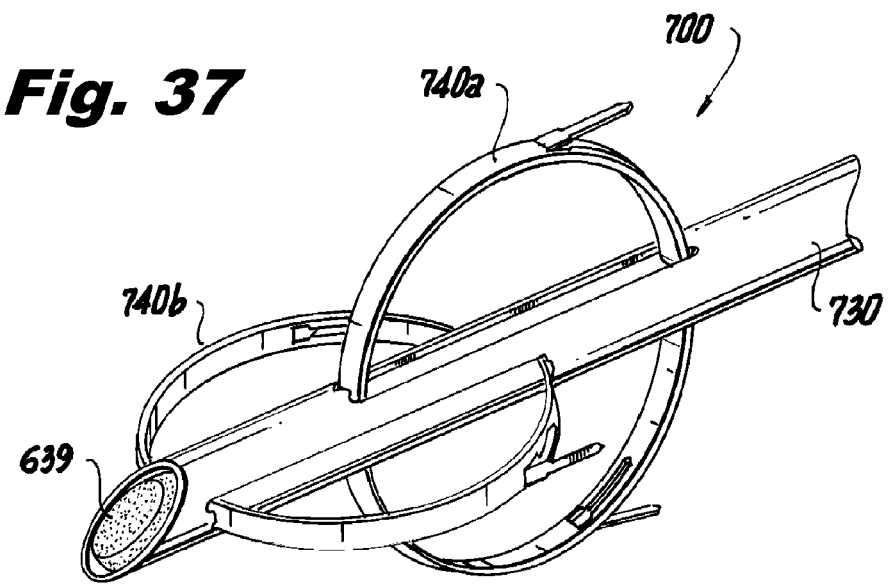
FIG. 37 is an isometric view of a distal end portion of a further embodiment of a surgical aspirator-retractor in accordance with the invention having deployable ribbon elements with barbs formed thereon to facilitate engagement with a hollow structure.

FIG. 37 is an isometric view of a distal end portion of a further embodiment of a surgical aspirator-retractor 700 in accordance with the invention having deployable ribbon elements 740a, 740b with barbs formed thereon to facilitate engagement with a hollow structure. Construction and operation of the aspirator-retractor 700 is in keeping with other embodiments described herein, such as with the embodiment of FIGS. 35 and 36.

Figure 38:
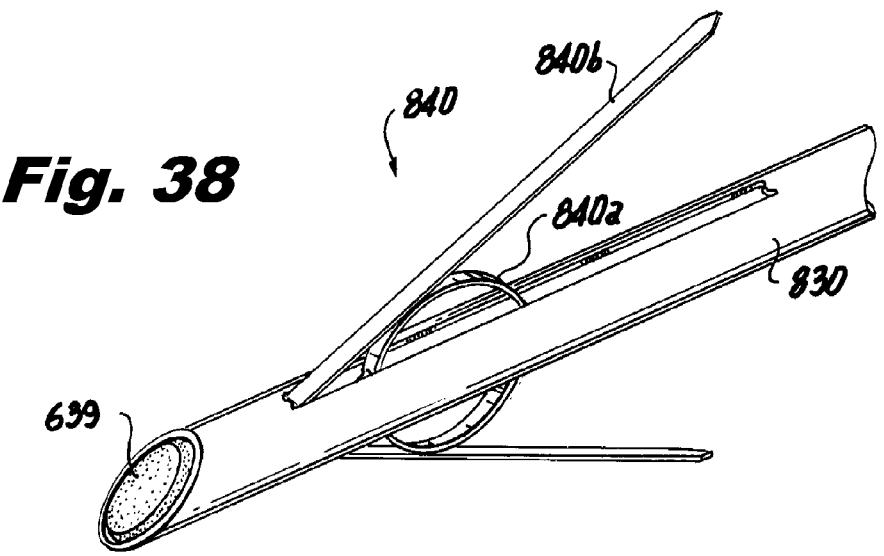
FIG. 38 is an isometric view of a distal end portion of still a further embodiment of a surgical aspirator-retractor in accordance with the invention having deployable ribbon elements for deploying respective elongated barbs.

FIG. 38 is an isometric view of a distal end portion of still a further embodiment of a surgical aspirator-retractor in accordance with the invention having a distal anchor element 840 formed by deployable ribbon elements 840a for deploying respective elongated barbs 840b.

Figure 39:
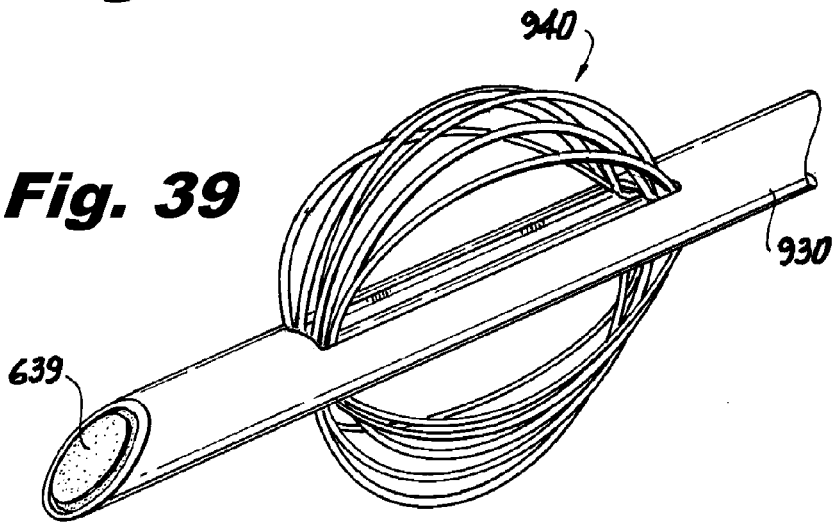
FIG. 39 is an isometric view of a distal end portion of still a further embodiment of a surgical aspirator-retractor in accordance with the invention, having an axial, radially deployable wire anchor.

FIG. 39 is an isometric view of a distal end portion of still a further embodiment of a surgical aspirator-retractor in accordance with the invention, having an axial, radially deployable wire anchor 940, deployable from the needle body 930 thereof. Deployment of the anchor 940 can be effected by providing distally-directed force to an actuating rod, connected to a proximal end of the wire anchor 940, and concentrically disposed within the lumen of the needle body 930.

Figure 40:
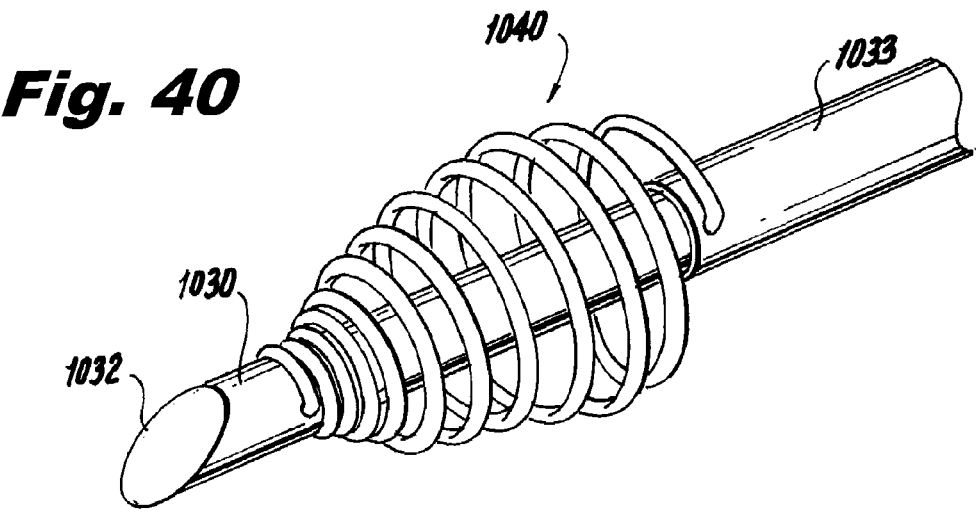
FIG. 40 is an isometric view of a distal end portion of another embodiment of a surgical aspirator-retractor in accordance with the invention, having a helical, radially deployable wire anchor.

FIG. 40 is an isometric view of a distal end portion of another embodiment of a surgical aspirator-retractor in accordance with the invention, having a helical, radially deployable wire anchor 1040. A distal portion of the helical wire anchor 1040 is secured to a main needle body 1030, while a proximal end portion of the helical wire anchor 1040 is secured to a concentrically outer actuating tube 1033. Therefore, relative movement between the main needle body 1030 and the outer tube 1033, including rotation and/or translation, can effect deployment of the anchor 1040. The distal end 1032 can be solid, or open, or can include apertures for aspiration on side surfaces thereof.

Figure 41:
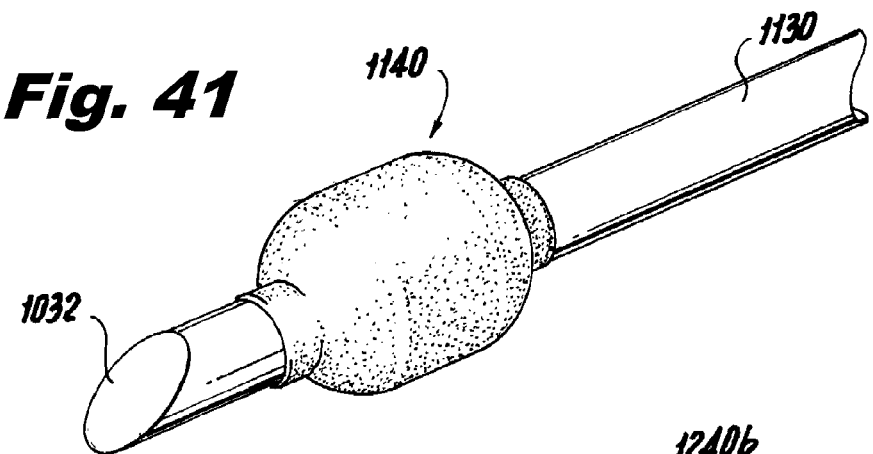
FIG. 41 is an isometric view of a distal end portion of another embodiment of a surgical aspirator-retractor in accordance with the invention, having a single inflatable distal anchor element.

FIG. 41 is an isometric view of a distal end portion of another embodiment of a surgical aspirator-retractor in accordance with the invention, having a single inflatable distal anchor element 1140 carried by a needle body 1130. The inflatable distal anchor element 1140 can be inflated via one or more channels formed within the needle body 1130, and configured and adapted to be insufflated by a liquid, such as saline, or a gas, such as compressed air or carbon dioxide. As with any of the embodiments described herein, the distal end 1032 can be solid, or open, or can include apertures for aspiration on side surfaces thereof.

Figure 42:
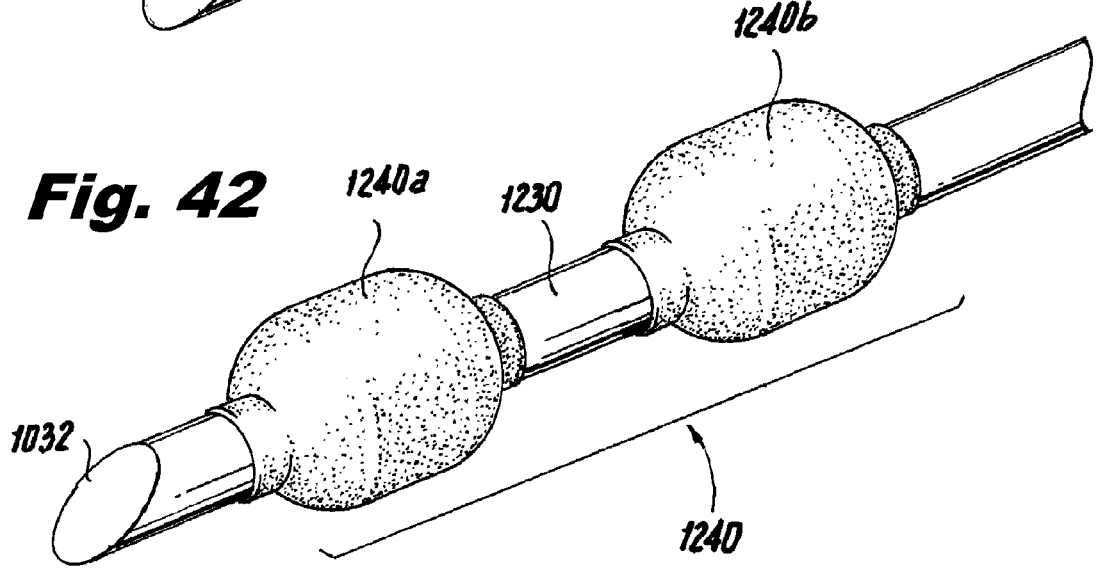
FIG. 42 is an isometric view of a distal end portion of a further embodiment of a surgical aspirator-retractor in accordance with the invention, having a plurality of inflatable distal anchor elements, for respectively engaging inner and outer surfaces of a hollow organ, such as a the gallbladder.
Figure 48:
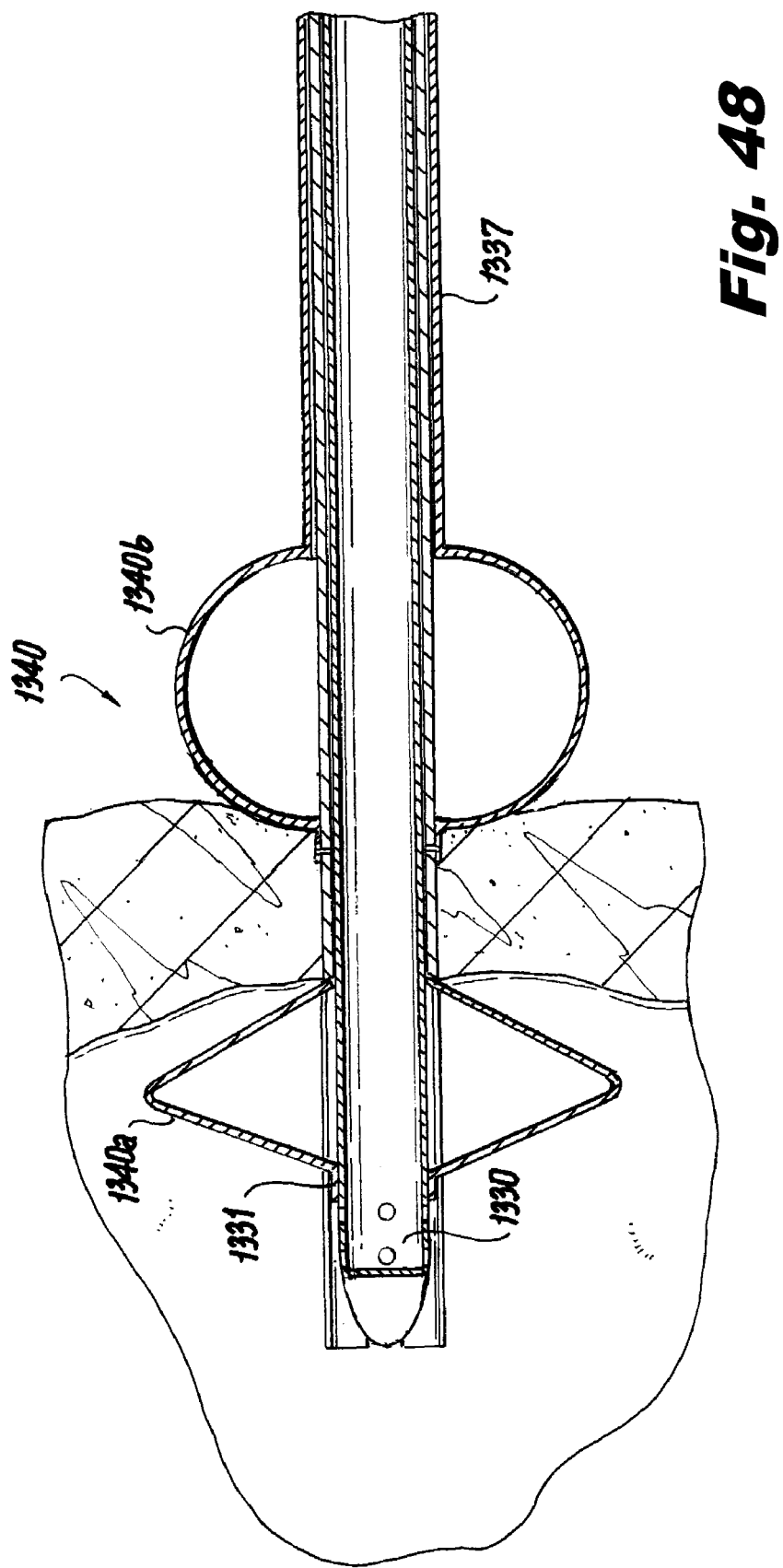

FIG. 42 is an isometric view of a distal end portion of a further embodiment of a surgical aspirator-retractor in accordance with the invention, having a plurality of inflatable distal anchor elements 1240a, 1240b, provided on a needle body 1230, for respectively engaging inner and outer surfaces of a hollow organ, such as a the gallbladder. The inflatable anchor elements 1240 can be inflated via one or more channels formed within the needle body 1230, and configured and adapted to be insufflated by a liquid, such as saline, or a gas, such as compressed air or carbon dioxide. As with any of the embodiments described herein, the distal end 1032 can be solid, or open, or can include apertures for aspiration on side surfaces thereof.

FIGS. 43-48 illustrate various views of still a further embodiment of a surgical aspirator-retractor in accordance with the present invention having a distal anchor 1340 with axially offset pairs of outwardly expanding anchor portions 1340a, 1340b, formed of ribbons of material, for engaging inner and outer wall surfaces of a hollow organ, respectively, as described above in connection with other embodiments. In accordance with this embodiment, a moveable inner shaft 1331 is provided over the needle body 1330, over which a stationary intermediate shaft 1333 is provided, over which a moveable outer shaft 1337 is provided. Each of the moveable shafts is controllable, with respect to the stationary main needle body 1330 and intermediate shaft 1333. In accordance with the invention, distally-directed compressive forces result in radial outward expansion of the respective anchor portions 1340a, 1340b. As with any of the embodiments described herein, apertures 1337 for aspiration can be provided on side surfaces of the needle body 1330.

Figure 49:
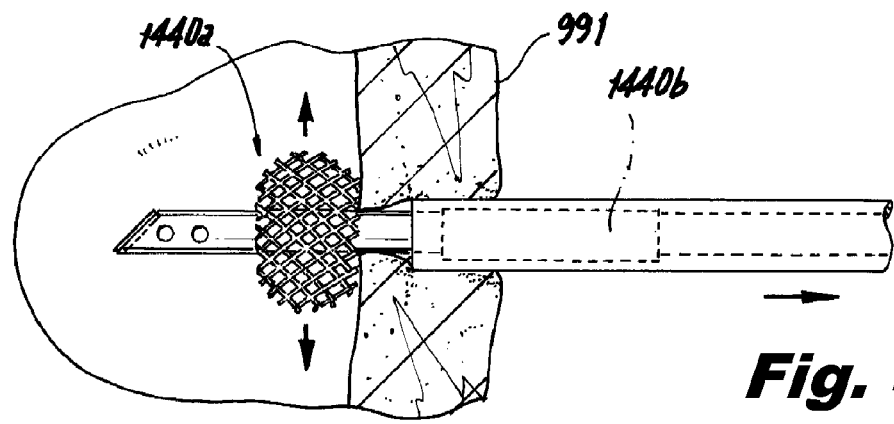
FIG. 49 is a side view of a distal end portion of still a further embodiment of a surgical aspirator-retractor in accordance with the invention, having two expandable mesh distal anchor elements, with the distalmost anchor deployed.

FIG. 49 is a side view of a distal end portion 1440a of still a further embodiment of a surgical aspirator-retractor in accordance with the invention, having an expandable mesh distal anchor elements.

Figure 50:
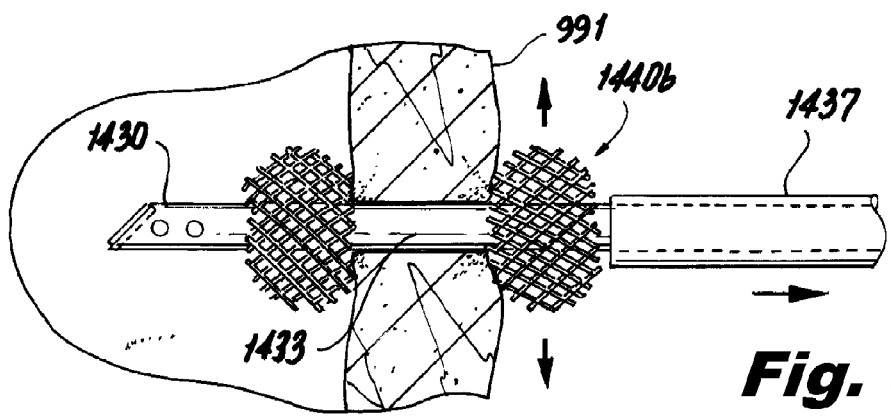
FIG. 50 is a side view of a distal end portion of the surgical aspirator—of FIG. 49, having a pair of expandable mesh distal anchor elements, with both anchor elements deployed.

FIG. 49 is a side view of a distal end portion of still a further embodiment of a surgical aspirator-retractor in accordance with the invention, having two expandable mesh distal anchor elements 1440a, 1440b, with the distalmost anchor 1440a in a deployed, expanded conformation. FIG. 50 is a side view of the surgical aspirator of FIG. 49, with both anchor elements deployed, sandwiching a wall of the gallbladder therebetween. As with other embodiments, the mesh distal anchor elements 1440a, 1440b are connected to coaxial elements to permit manipulation thereof.

Figure 51:
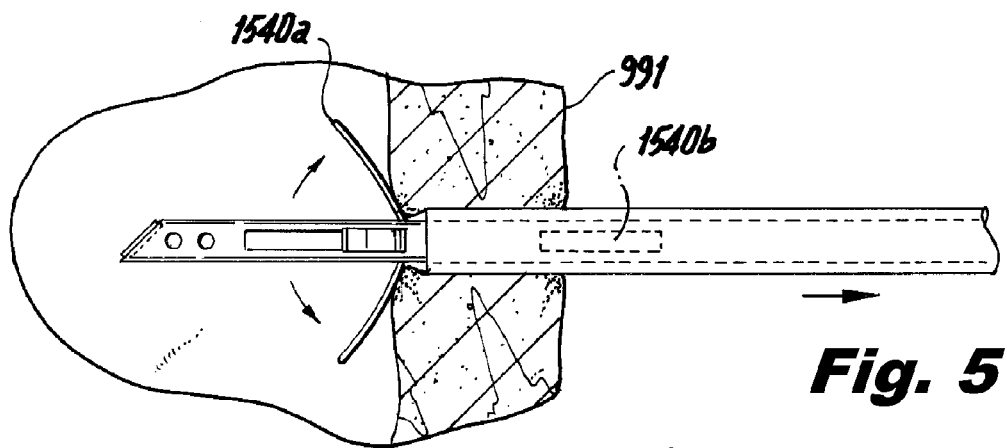
FIG. 51 is a side view of a distal end portion of a surgical aspirator-retractor having distal and proximal prong-shaped engagement elements, with only inner anchor elements deployed.
Figure 52:
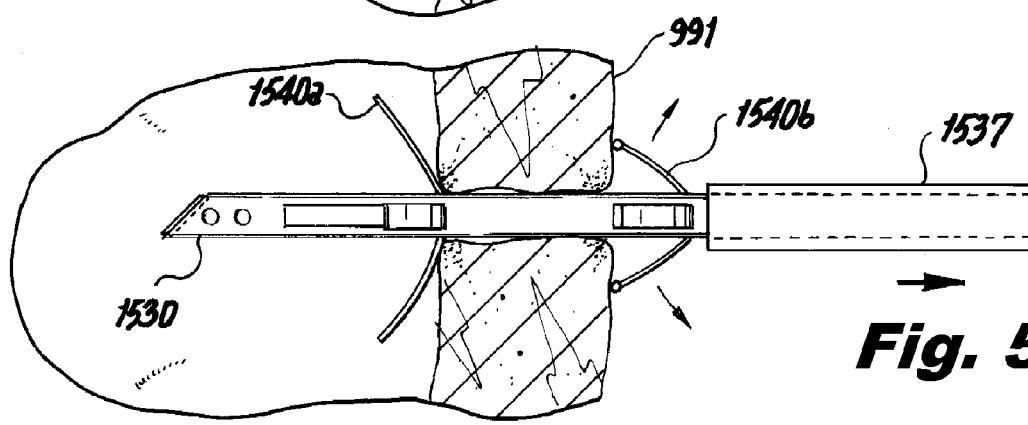
FIG. 52 is a side view of a distal end portion of the surgical aspirator-retractor of FIG. 51 with both inner and outer anchor elements deployed.

FIG. 51 is a side view of a distal end portion of the surgical aspirator-retractor having proximal and distal prong-shaped anchor elements 1540a, 1540b, with only distal anchor elements 1540a deployed. FIG. 52 is a side view of the surgical aspirator-retractor of FIG. 51 with both inner (distal) 1540a and outer (proximal) 1540b anchor elements deployed. An outer sheath 1537 is provided to facilitate stowing of the anchor elements when retraction is completed.

Figure 53:
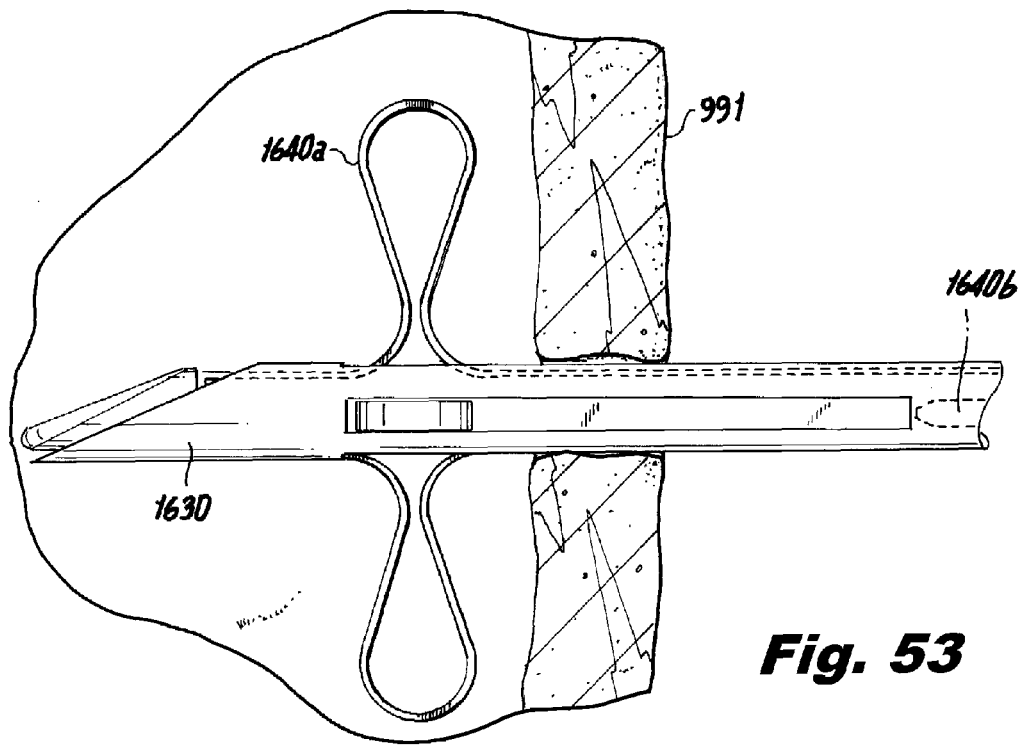
FIG. 53 is a side view of a distal end portion of an additional embodiment of a surgical aspirator-retractor in accordance with the invention, having distal deployable ribbon-shaped engagement elements.
Figure 54:
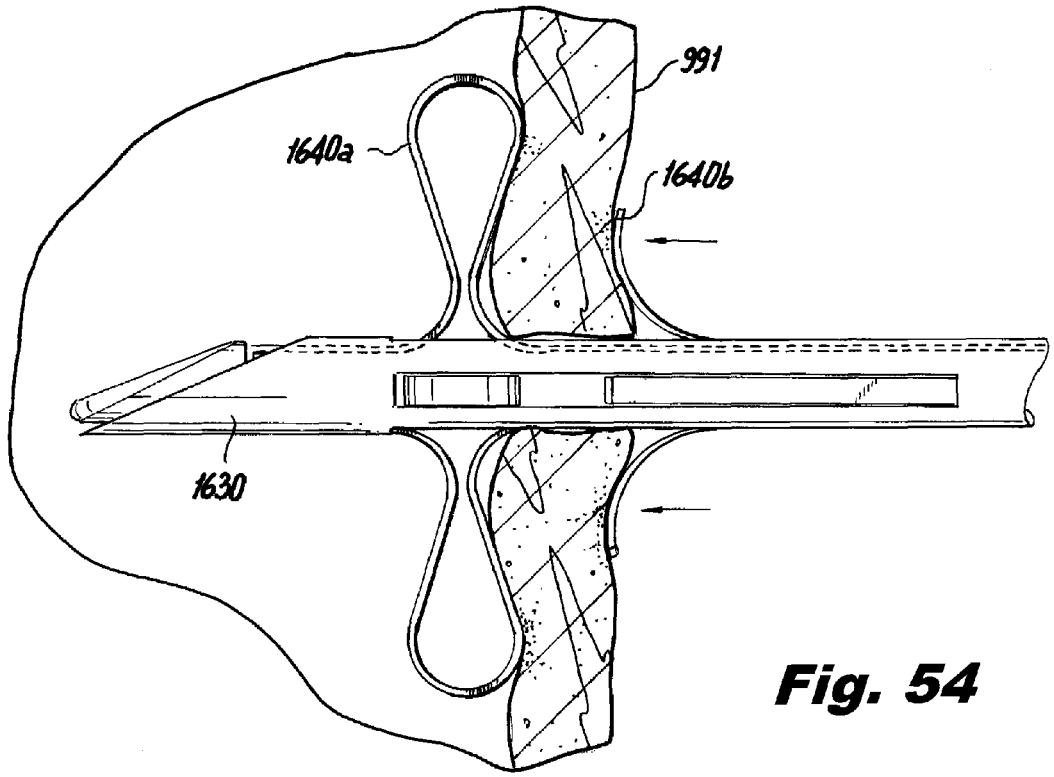
FIG. 54 is a side view of a distal end portion of the surgical aspirator-retractor of FIG. 53, having distal deployable ribbon-shaped engagement elements and proximal deployable prong-shaped engagement elements, with all elements in a deployed configuration.

FIG. 53 is a side view of a distal end portion of an additional embodiment of a surgical aspirator-retractor in accordance with the invention, having distal deployable ribbon-shaped engagement elements 1640a, and proximal deployable prong-shaped engagement elements 1640b, adapted and configured for deployable from common slots provided in the needle body 1630. FIG. 54 is a side view illustrating all anchor elements in a deployed configuration, thereby sandwiching the wall of the gallbladder 991 therebetween.

It will be apparent to those skilled in the art that various modifications and variations can be made in the device and method of the present invention without departing from the spirit or scope of the invention. It is particularly conceived that elements of one embodiment described herein can advantageously be applied to any embodiment of devices in accordance with the invention, even if such features are not explicitly described in connection therewith, unless such feature should be mutually exclusive or otherwise incompatible with other features of such embodiment. Thus, it is intended that the present invention include modifications and variations that are within the scope of the appended claims and their equivalents.

What is claimed is:

1. A surgical instrument for laparoscopic procedures, adapted and configured to aspirate and retract a hollow organ, comprising:
a needle body defining an aperture adapted and configured for aspirating contents of the hollow organ, the needle body including a sharpened distal tip;
an outer shaft operatively disposed radially outward of the needle body and longitudinally translatable relative thereto; and
an anchor, having a proximal end mounted to the outer shaft and a distal end mounted to the needle body,
wherein the anchor is mounted for deployment from a collapsed configuration to an expanded deployed configuration for engaging and retracting the hollow organ by relative longitudinal translation of the needle body an outer shaft, and
wherein the distal end of the anchor is attached to an outer surface of the needle body such that the sharpened distal tip extends beyond the distal end of the anchor in both the collapsed and the expanded deployed configurations.

2. The surgical instrument of claim 1, wherein the aperture in the needle body is operatively disposed between the proximal and distal ends of the anchor in both the collapsed and expanded deployed configurations.

3. The surgical instrument of claim 1, wherein the distal end of the anchor is longitudinally fixed relative to an outside surface of the needle body.

4. The surgical instrument of claim 1, wherein the anchor is a deployable cage structure.

5. The surgical instrument of claim 4, wherein the cage structure is spring-biased such that the cage structure is deployed by tension provided in a spring when the cage structure extends beyond the needle body by a predetermined distance.

6. The surgical instrument of claim 4, wherein the cage structure includes at least one barb configured to extend from the cage structure when the cage structure is in the deployed configuration.

7. The surgical instrument of claim 6, wherein barb is distally directed to facilitate reinsertion of the cage structure into a lumen of the needle body.

8. The surgical instrument of claim 6, wherein the at least one barb is proximally directed to facilitate engagement thereof with an inner wall of the hollow organ.

9. The surgical instrument of claim 8, wherein the cage is configured so that the at least one barb is substantially parallel to the needle body and surrounding portions of the cage in the collapsed configuration.

10. The surgical instrument of claim 4, wherein the cage structure is provided with at least one fenestration to facilitate bending manipulation of the cage.

11. The surgical instrument of claim 4, wherein the cage structure is provided with a plurality of legs, symmetrically arranged about a longitudinal axis of the surgical instrument.

12. The surgical instrument of claim 4, wherein the cage structure includes a plurality of nested cages to permit flexibility of the cage.

13. The surgical instrument of claim 1, wherein the anchor is a deployable wire structure.

14. The surgical instrument of claim 1, wherein the anchor includes a distal anchor portion and a proximal anchor portion adapted and configured to engage inner and outer surfaces of the hollow organ, respectively.

15. The surgical instrument of claim 14, wherein the distal anchor portion and the proximal anchor portion are longitudinally spaced apart by a distance sufficient to permit engagement of a wall of the hollow organ.

16. The surgical instrument of claim 14, wherein the distal anchor portion and a proximal anchor portion are rotationally offset from one another by about 90 degrees, with respect to a longitudinal axis of the surgical instrument.

17. The surgical instrument of claim 14, wherein the distal anchor portion and the proximal anchor portion are of substantially the same configuration.

18. The surgical instrument of claim 1, further comprising a deployable tip protector to inhibit unintentional injury by the sharpened distal tip of the needle body.

19. The surgical instrument of claim 18, wherein the deployable tip protector is a translatable sheath adapted and configured to be deployed over the sharpened distal tip of the needle body.

20. The surgical instrument of claim 18, wherein the deployable tip protector is a translatable plug adapted and configured to be deployed from within a lumen of the needle body.

21. The surgical instrument of claim 20, wherein the plug is adapted and configured to extend distally beyond the sharpened distal tip of the needle body, to inhibit piercing of a structure by the needle body, when in a deployed position.

22. The surgical instrument of claim 1, wherein the aperture is provided at the distal end of the body.

23. The surgical instrument of claim 1, wherein the aperture is provided in a distal end portion of a sidewall of the body.

24. The surgical instrument of claim 1, wherein the anchor is formed at least in part from one of a shape-memory alloy and a stainless steel.

25. The surgical instrument of claim 1, when in the anchor is formed at least in part by laser cutting.

26. The surgical instrument of claim 1, wherein an outer diameter of the needle body is about 2 mm.

27. The surgical instrument of claim 1, wherein the anchor is configured such that, in the deployed configuration, a width, measured transverse to a longitudinal axis thereof, is a maximum of about eight times that of a width in the collapsed configuration, measured transverse to the longitudinal axis thereof.

28. The surgical instrument of claim 1, wherein the needle body is provided with a sharpened end surface angled at about 15 degrees with respect to a longitudinal axis of the needle body.

29. The surgical instrument of claim 1, further comprising a handle in connection therewith, to facilitate manipulation of the surgical instrument.

30. The surgical instrument of claim 1, wherein the needle body includes a side surface having a plurality of apertures for aspiration.

31. A method of retracting a hollow organ comprising the steps of:
providing the surgical instrument of claim 1,
inserting the needle body of the surgical instrument through an abdominal wall of a patient;
inserting the needle body of the surgical instrument through a wall of the hollow organ;
aspirating the contents from the hollow organ;

deploying the first anchor of the surgical instrument within the hollow organ, to engage an inner surface of the hollow organ; and retracting the hollow organ.

32. The method of claim 31, further comprising the step of: deploying a second anchor portion of the surgical instrument outside the hollow organ to engage an outer surface of the hollow organ.

33. A surgical instrument for laparoscopic procedures, adapted and configured to aspirate and retract a gallbladder, comprising:

means for aspirating contents from a gallbladder, the means for aspirating including an aperture defined by a needle of the surgical instrument, the needle including a sharpened distal tip; and means for engaging and retracting and stabilizing the gallbladder, the means for engaging and retracting and stabilizing including an outer shaft longitudinally translatable relative to the needle, an anchor mounted to the needle and the outer shaft such that distal longitudinal translation of the outer shaft relative to the needle moves the anchor from a collapsed configuration to an expanded deployed configuration for engaging and retracting and stabilizing the gallbladder, the anchor having a proximal end mounted to the outer shaft and a distal end mounted to the needle, wherein the distal end of the anchor is attached to an outer surface of the needle such that the sharpened distal tip extends beyond the distal end of the anchor in both the collapsed and the expanded deployed configurations.

34. A surgical instrument manufactured by a process comprising the steps of:

providing a tubular needle with a lumen extending therethrough and a sharpened distal tip;

machining a deployable anchor;

machining and mounting an outer shaft concentrically and radially outward of the needle body such that the tubular needle and outer shaft are longitudinally translatable relative to one another;

mounting the deployable anchor to the needle and the outer shaft such that relative longitudinal translation of the outer shaft and needle causes the anchor to move between a radially collapsed configuration and an expanded deployed configuration wherein the mounting the deployable anchor includes attaching a distal end of the anchor to an outer surface of the needle such that the sharpened distal tip extends beyond the distal end of the anchor in both the radially collapsed and the expanded deployed configurations.

* * * * *